(12) United States Patent
Hanakawa et al.

(10) Patent No.: US 9,630,027 B2
(45) Date of Patent: Apr. 25, 2017

(54) BEAM TRANSPORT SYSTEM AND PARTICLE BEAM THERAPY SYSTEM

(71) Applicant: MITSUBISHI ELECTRIC CORPORATION, Chiyoda-ku, Tokyo (JP)

(72) Inventors: Kazushi Hanakawa, Tokyo (JP); Kengo Sugahara, Tokyo (JP); Shuhei Odawara, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/891,922

(22) PCT Filed: Jul. 11, 2013

(86) PCT No.: PCT/JP2013/068981
§ 371 (c)(1),
(2) Date: Nov. 17, 2015

(87) PCT Pub. No.: WO2015/004772
PCT Pub. Date: Jan. 15, 2015

(65) Prior Publication Data
US 2016/0144202 A1    May 26, 2016

(51) Int. Cl.
*A61N 5/10* (2006.01)
*H05H 7/04* (2006.01)
*H05H 7/00* (2006.01)

(52) U.S. Cl.
CPC ......... *A61N 5/1064* (2013.01); *A61N 5/1077* (2013.01); *H05H 7/001* (2013.01);
(Continued)

(58) Field of Classification Search
None
See application file for complete search history.

(56) References Cited

U.S. PATENT DOCUMENTS

| 4,191,887 A | 3/1980 | Brown |
| 4,795,912 A | 1/1989 | Maschke |

(Continued)

FOREIGN PATENT DOCUMENTS

| JP | 54-152386 A | 11/1979 |
| JP | 07-275381 A | 10/1995 |

(Continued)

OTHER PUBLICATIONS

International Search Report (PCT/ISA/210) mailed on Oct. 15, 2013, by the Japanese Patent Office as the International Searching Authority for International Application No. PCT/JP2013/068981.

*Primary Examiner* — Jack Berman
(74) *Attorney, Agent, or Firm* — Buchanan Ingersoll & Rooney PC

(57) ABSTRACT

In a beam transport system, based on a beam temporal-variation related amount that has been calculated by a beam analyzer and that is a beam-position temporal variation amount or a beam diameter at a beam profile monitor, an optical parameter calculator calculates a start-point momentum dispersion function that is a momentum dispersion function ($\eta$, $\eta'$) of a charged particle beam at a start point in design of the beam transport system that is set on a beam trajectory of the accelerator; and calculates optical parameters using, as an initial condition, the start-point momentum dispersion function and a beginning condition at an irradiation position at the time of detecting profile data.

18 Claims, 8 Drawing Sheets

(52) U.S. Cl.
CPC ....... *H05H 7/04* (2013.01); *A61N 2005/1087* (2013.01); *H05H 2007/002* (2013.01); *H05H 2007/048* (2013.01)

(56) References Cited

U.S. PATENT DOCUMENTS

| | | | |
|---|---|---|---|
| 6,774,378 B1* | 8/2004 | Huang | H05H 7/04 250/492.2 |
| 9,132,285 B2* | 9/2015 | Takayanagi | A61N 5/1071 |
| 9,289,624 B2* | 3/2016 | Jongen | A61N 5/10 |
| 9,387,346 B2* | 7/2016 | Hanakawa | A61N 5/1043 |
| 2011/0101236 A1 | 5/2011 | Cameron et al. | |
| 2016/0279446 A1* | 9/2016 | Tachibana | A61N 5/1043 |

FOREIGN PATENT DOCUMENTS

| | | |
|---|---|---|
| JP | 11-176596 A | 7/1999 |
| JP | 2011-206237 A | 10/2011 |
| WO | WO 2011/053960 A1 | 5/2011 |

\* cited by examiner

BEAM TRANSPORT SYSTEM AND PARTICLE BEAM THERAPY SYSTEM

TECHNICAL FIELD

The present invention relates to a beam transport system that transports a charged particle beam formed of charged particles, such as protons, heavy particles, etc., and a particle beam therapy system that radiates the transported charged particle beam to an object to be irradiated, such as an article, a human body, etc.

BACKGROUND ART

Generally, a particle beam therapy system includes a beam generation apparatus that generates a charged particle beam; an accelerator that is connected to the beam generation apparatus and accelerates the generated charged particle beam; a charged particle-beam transport system that transports the charged particle beam emitted after accelerated up to a specified energy by the accelerator; and a particle beam irradiation apparatus that is placed at the downstream side of the beam transport system, for radiating the charged particle beam to an irradiation target.

As to the beam transport system, generally, its optical parameters are designed while setting two reference points at one point on the beam trajectory of the accelerator and at a beam irradiation position (isocenter). The one point on the beam trajectory of the accelerator is given as a start point in the optical parameter design, and the beam irradiation position, in particular, the isocenter which is the center of that position, is given as a terminal point in the optical parameter design. Specifically, the beam transport system transports the beam so that the beam reaches the irradiation position, in such a manner that the intensity of each electromagnet in said beam transport system is calculated using, as a design value, a beam initial condition at a communication point (start point) between the accelerator and the beam transport system (High Energy Beam Transport System (HEBT System)), followed by setting that intensity (excitation current) to the electromagnet.

When the accelerator is a small-size medical synchrotron, because of an unexpected magnetic field by the electromagnets of the synchrotron (a magnetic field generated due to machining error, etc.), there are cases where, even if the initial value of the synchrotron is an ideal value (design value), the Hardt condition is not satisfied even when a six-pole electromagnet is properly arranged, so that a separatrix branch for emission differs depending on the energy. Thus, there is a phenomenon (chromatic aberration) in which, an angle (inclination) or position of the beam at the communication point differs depending on an amount of the energy, so that, though depending on a beam emission method of the accelerator, a phenomenon occurs in which the position of the beam moves or the diameter of the beam increases, at the irradiation position.

The reason of occurrence of the chromatic aberration, that is the phenomenon in which a difference emerges in the angle (inclination) or position of the beam, will be described. FIG. 15 is a graph illustrating a movement of the beam in a phase space at the start point, and FIG. 16 is diagrams each illustrating beam trajectories. In FIG. 15, the abscissa represents a distance ΔX in an x-direction perpendicular to the central axis of the beam trajectories, and the ordinate represents an inclination ΔX' at ΔX relative to the central axis of the beam trajectories. In FIG. 16, the abscissa represents an s-axis extending in a beam traveling direction, and the ordinate represents the distance ΔX in the x-direction. In FIG. 16, there are shown positions of bending electromagnets 63 and quadrupole electromagnets 64 each related to a change in beam trajectory, and a start point S and a terminal point T. Shown at the upper side in FIG. 16 is in an ideal case of beam emission, and shown at the lower side in FIG. 16 is in a case where the beam emission is deviated from the ideal one.

Heretofore, a beam optical system in the beam transport system has been designed on the assumption that there is no movement of the beam at the start point S, and on the presumption that the beam has an assumed-phase spatial distribution shown as an ellipse in FIG. 15. However, an actual beam has phase spatial distributions 60 due to temporal change in phase spatial distribution as shown at 61a, 61b and 61c. As to the actual beam, its current value intermittently goes back and forth between zero and a value other than zero as shown in FIG. 5, so that the phase spatial distribution of the beam differs among at Times t1, t2 and t3. For example, a phase spatial distribution of the beam is: the phase spatial distribution 61a at Time t1 (at the beginning of the spill); the phase spatial distribution 61b at Time t2 (at the middle of the spill); and the phase spatial distribution 61c at Time t3 (at the end of the spill).

In the ideal case of beam emission, as shown at the upper side in FIG. 16, even with no movement of the beam in the phase space at the start point S, variations occur at the upstream side as indicated by beam trajectories 65a, 65b and 65c; nevertheless, in the downstream side, adjustment of the excitation currents of the bending electromagnets 63 and the quadrupole electromagnets 64 makes it possible to adjust the beam trajectories to be matched to the beam axis (s-axis) so that no chromatic aberration occurs at the terminal point T. However, in the case where the beam emission is deviated from such an ideal state, namely, in the case where the phase spatial distribution varies temporally, as shown at the lower side in FIG. 16, even at the downstream side, variations occur as indicated by beam trajectories 66a, 66b and 66c, so that a chromatic aberration occurs at the terminal point T as an irradiation position. For example, the beam trajectory 66a is a trajectory corresponding to the phase spatial distribution 61a, the beam trajectory 66b is a trajectory corresponding to the phase spatial distribution 61b, and the beam trajectory 66c is a trajectory corresponding to the phase spatial distribution 61c. In the case where the beam emission is deviated from the ideal state, because of the occurrence of the chromatic aberration at the terminal point T, the beam diameter becomes enlarged and the beam position (gravity-center position) becomes placed apart from the beam axis (s-axis).

In an actual beam transport system, there is a temporal variation in the phase spatial distribution of the beam at the start point S, so that if no consideration is paid to the temporal variation in the phase spatial distribution of the beam, a chromatic aberration occurs at the terminal point T as described above. Thus, in order to nullify the chromatic aberration at the terminal point T, it is necessary to take into consideration the temporal variation in the phase spatial distribution of the beam at the start point S.

In Patent Document 1, there is described a method for accomplishing automated adjustment of the beam size in order to make adjustment of the beam size easier. The charged-particle beam transport apparatus of Patent Document 1 includes: a sensitivity calculator that calculates a sensitivity matrix indicative of a relationship of a beam size relative to a converging force of a beam focusing device such as a quadrupole electromagnet, etc., on the basis of the beam sizes and beam profiles measured by a plurality of profile monitors placed between the outlet of the accelerator and the inlet of the irradiation apparatus; and an excitation-current correction-amount calculator that calculates using the sensitivity matrix, a beam-converging force from a target value set for adjusting the beam size; so that the beam focusing device is controlled using the excitation current calculated by the excitation-current correction-amount calculation device. According to the adjustment method of the beam size in Patent Document 1, the sensitivity matrix is calculated from the beam sizes and the beam profiles measured by the profile monitors after rough adjustment for the beam transportation, the excitation current of each beam focusing device is calculated using the sensitivity matrix, and then an adjustment is performed by exciting said each beam focusing device using the excitation current. This method is repeated until the beam size becomes sufficiently near to an intended value.

CITATION LIST

Patent Document

Patent Document 1: Japanese Patent Application Laid-open No. 2011-206237 (Paragraph 0037 to Paragraph 0049, paragraph 0057 to Paragraph 0061, FIG. 1, FIG. 3)

SUMMARY OF THE INVENTION

Problems to be Solved by the Invention

According to the charged-particle beam transport apparatus (corresponding to a beam transport system) in Patent Document 1, the adjustment of the beam size is achieved by repeating such an adjustment in which the excitation current of each beam focusing device is calculated using the sensitivity matrix calculated from the beam sizes measured by the profile monitors and then said each beam focusing device is excited using this excitation current, so as to cause the beam size to be sufficiently near to the intended value. However, according to the charged-particle beam transport apparatus in Patent Document 1, no consideration is paid to a chromatic aberration at the start point and the terminal point in the optical parameter design. Thus, even if the beam size measured by the profile monitor on the beam-transport pathway can be set to the intended value, it is unable to nearly nullify a chromatic aberration of the beam at the irradiation position. Further, in the case with a small-sized synchrotron, as described previously, it is difficult to nullify a chromatic aberration at the start point in the optical parameter design of the beam transport system, so that when the method for adjustment of the beam size in Patent Document 1 is applied to the small-sized synchrotron, the number of repetition times for beam adjustment increases. According to the method for adjustment of the beam size in Patent Document 1, even if the beam adjustment could be achieved, there is a problem after all that it is unable to nearly nullify the chromatic aberration of the beam at the irradiation position.

In the case with the small-sized synchrotron and if going to nullify the chromatic aberration at the start point in the optical parameter design of the beam transport system, it is necessary to use a high-performance bending electromagnet, quadrupole electromagnet or six-pole electromagnet. This brings enlargement or complexity of the accelerator or the beam transport system, thus causing a problem that the accelerator or the beam transport system becomes expensive.

This invention has been made to solve the problems as described above, and an object thereof is to provide a beam transport system that can nearly nullify the chromatic aberration of the beam at the irradiation position of the beam even when it is a beam emitted from a small-sized synchrotron.

Means for Solving the Problems

A beam transport system according to the invention comprises: at least one bending electromagnet that deflects a charged particle beam; at least two quadrupole electromagnets that focus or defocus the charged particle beam; at least one beam profile monitor that detects profile data of the charged particle beam; a beam analyzer that calculates based on the profile data, a beam temporal-variation related amount that is a beam-position temporal variation amount or a beam diameter, at the beam profile monitor; an optical parameter calculator that calculates optical parameters of the beam transport system; and an electromagnet power source that sets an excitation current of each of the bending electromagnet and the quadrupole electromagnets, based on the optical parameters calculated by the optical parameter calculator. The optical parameter calculator of the beam transport system according to the invention is characterized in that: it calculates based on the beam temporal-variation related amount, a start-point momentum dispersion function that is a momentum dispersion function of the charged particle beam at a start point in design of the beam transport system that is set on a beam trajectory of an accelerator; and it calculates said optical parameters using, as an initial condition, the start-point momentum dispersion function and a beginning condition at an irradiation position at the time of detecting the profile data.

Effect of the Invention

In accordance with the beam transport system according to the invention, excitation currents of the bending electromagnet and the quadrupole electromagnets are set based on the optical parameters that are calculated using, as the initial condition, the start-point momentum dispersion function of the charged particle beam at the start point in design, said function being based on the beam temporal-variation related amount, and the beginning condition at the irradiation position at the time of detecting the profile data, so that it is possible to nearly nullify the chromatic aberration of the beam at the irradiation position of the beam even when it is a beam emitted from a small-sized synchrotron.

MODES FOR CARRYING OUT THE INVENTION

Embodiment 1

Figure 1:
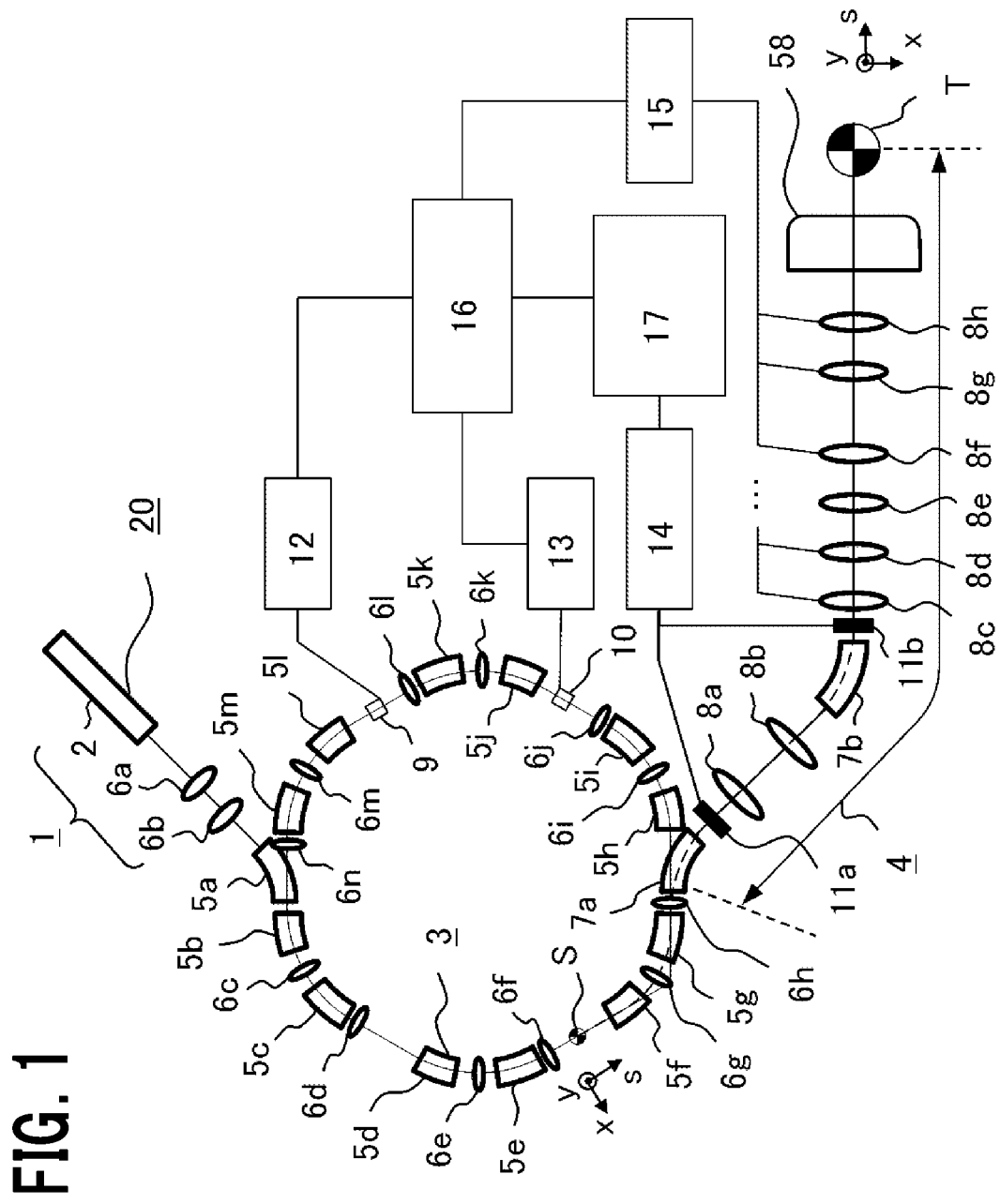
FIG. 1 is a schematic configuration diagram of a particle beam therapy system according to the invention.
Figure 2:
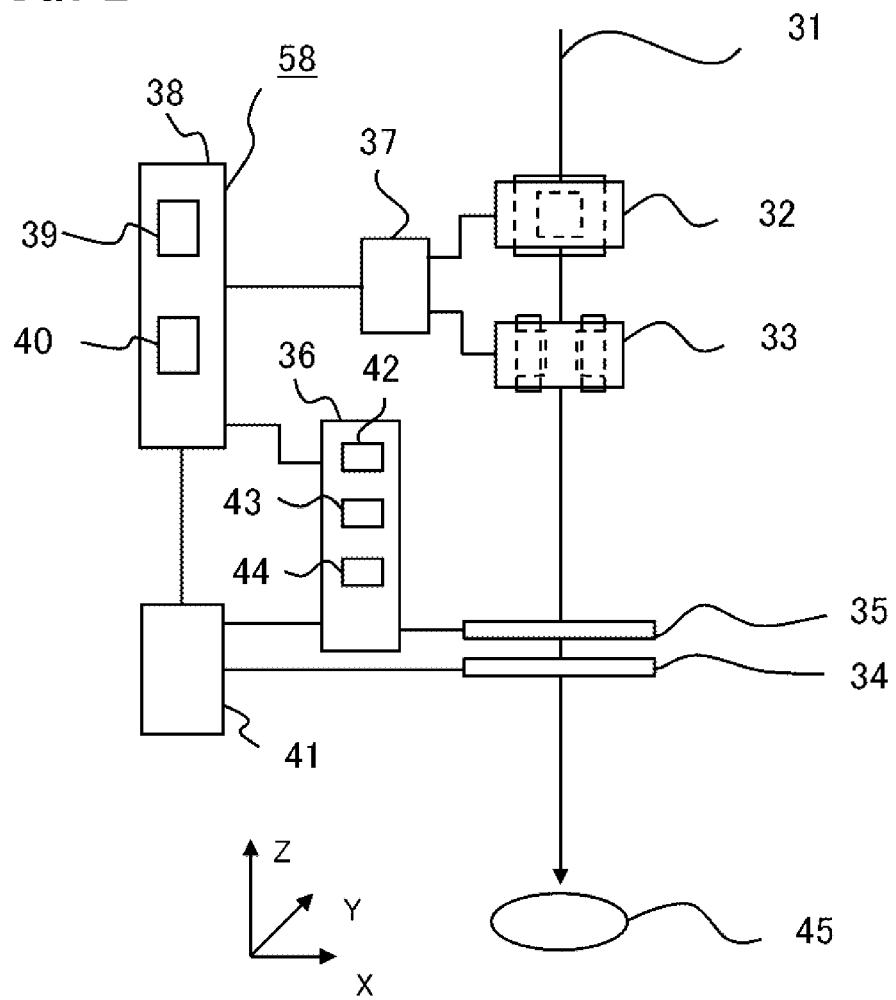
FIG. 2 is a diagram showing a configuration of a particle beam irradiation apparatus in FIG. 1.

FIG. 1 is a schematic configuration diagram of a particle beam therapy system according to the invention, and FIG. 2 is a diagram showing a configuration of a particle beam irradiation apparatus according to the invention. A particle beam therapy system 20 includes an injection system 1, an accelerator 3, a beam transport system 4 and a particle beam irradiation apparatus 58. The injection system 1 has an injector 2 and quadrupole electromagnets 6a, 6b. The accelerator 3 includes: a plurality of bending electromagnets 5a, 5b, 5c, 5d, 5e, 5f, 5g, 5h, 5i, 5j, 5k, 5l, 5m; a plurality of quadrupole electromagnets 6c, 6d, 6e, 6f, 6g, 6h, 6i, 6j, 6k, 6l, 6m, 6n; an acceleration cavity 9; an x-direction kick electrode 10; an RF-acceleration power source 12; an RF-kick power source 13; and a device controller 16. The beam transport system 4 has: a plurality of bending electromagnets 7a, 7b; a plurality of quadrupole electromagnets 8a, 8b, 8c, 8d, 8e, 8f, 8g, 8h; beam profile monitors 11a, 11b; a beam analyzer 14; an electromagnet power source 15; and an optical parameter calculator 17. For the quadrupole electromagnets in the injection system 1 and the accelerator 3, numeral 6 is used collectively, and numerals 6a to 6n are used when they are to be described distinctively. For the bending electromagnets in the accelerator 3, numeral 5 is used collectively, and numerals 5a to 5m are used when they are to be described distinctively. For the bending electromagnets in the beam transport system 4, numeral 7 is used collectively, and numerals 7a, 7b are used when they are to be described distinctively. For the quadrupole electromagnets in the beam transport system 4, numeral 8 is used collectively, and numerals 8a to 8h are used when they are to be described distinctively. For the beam profile monitor, numeral 11 is used collectively, and numerals 11a, 11b are used when they are to be described distinctively.

The bending electromagnets 5, 7 deflect the charged particle beam, and the quadrupole electromagnets 6, 8 focus or defocus the charged particle beam. As to a beam coordinate system of the charged particle beam, an axis in the traveling direction of the charged particle beam (s-direction) is referred to as an s-axis, an axis in an x-direction that is perpendicular to the s-axis and that extends outwardly in a plane of the circular trajectory in the accelerator 3 is referred to as an x-axis, and an axis in a y-direction that is perpendicular to the s-axis and the x-axis is referred to as a y-axis. The acceleration cavity 9 accelerates the charged particle beam circulating in the accelerator 3. The x-direction kick electrode 10 is an electrode for pushing out using an electric field, the charged particle beam from the circulating direction to the outer circumferential side (x-direction) in order to emit the beam toward the beam transport system 4. The beam profile monitors 11 each detect beam-profile data for calculating the beam position, the beam size, etc. of the charged particle beam. The beam transport system 4 transports the charged particle beam to an irradiation position T through the particle beam irradiation apparatus 58.

The charged particle beam, that is a particle beam such as a proton beam or the like generated by an ion source of the injector 2, is accelerated by an pre-accelerator of the injector 2, and then the charged particle beam is injected into the accelerator 3 while being focused or defocused by the quadrupole electromagnets 6a, 6b. Here, description about the accelerator 3 will be made using a synchrotron as an example. The charged particle beam is accelerated up to a given energy. The charged particle beam is then introduced from the bending electromagnet 7a placed in the accelerator 3 into the beam transport system 4, transported to the irradiation position T through the particle beam irradiation apparatus 58, and radiated to a diseased site that is an irradiation target 45 (see, FIG. 2) of a patient. The particle beam irradiation apparatus 58 radiates the charged particle beam to the irradiation target 45 (see, FIG. 2) while enlarging the beam and/or scanning the beam so as to form an intended irradiation field.

In FIG. 2, the particle beam irradiation apparatus 58 includes: an X-direction scanning electromagnet 32 and a Y-direction scanning electromagnet 33 which scan the charged particle beam 31, respectively in an X-direction and a Y-direction that are directions perpendicular to the charged particle beam 31; a position monitor 34; a dose monitor 35; a dose-data converter 36; a beam-data processing device 41; a scanning-electromagnet power source 37; and an irradiation management device 38 for controlling the particle beam irradiation apparatus 58. The irradiation management device 38 includes an irradiation control computer 39 and an irradiation control device 40. The dose-data converter 36 includes a trigger generation unit 42, a spot counter 43 and an inter-spot counter 44. Note that in FIG. 2, the travelling direction of the charged particle beam 31 is a direction of −Z. Further, note that, although the −Z direction corresponds to the s-direction in the beam coordinate system, the X-direction and the Y-direction in FIG. 2 are not necessarily matched to the x-direction and the y-direction in the beam coordinate system.

The X-direction scanning electromagnet 32 is a scanning electromagnet for scanning the charged particle beam 31 in the X-direction, and the Y-direction scanning electromagnet 33 is a scanning electromagnet for scanning the charged particle beam 31 in the Y-direction. With respect to the charged particle beam 31 scanned by the X-direction scanning electromagnet 32 and the Y-direction scanning electromagnet 33, the position monitor 34 detects beam information for calculating a passing position (gravity center position) and a size of the beam that passes therethrough. The beam-data processing device 41 calculates the passing position (gravity center position) and the size of the charged particle beam 31 on the basis of the beam information that comprises a plurality of analog signals (pieces of beam information) detected by the position monitor 34. Further, the beam-data processing device 41 generates an abnormality detection signal indicative of a position abnormality and/or a size abnormality of the charged particle beam 31, and outputs the abnormality detection signal to the irradiation management device 38.

The dose monitor 35 detects the dose of the charged particle beam 31. The irradiation management device 38 controls the irradiation position of the charged particle beam 31 in the irradiation target 45 on the basis of treatment plan data prepared by an unshown treatment plan device, and moves the charged particle beam 31 to a next irradiation position when the dose having been measured by the dose monitor 35 and converted by the dose-data converter 36 into digital data, reaches a target dose. The scanning-electromagnet power source 37 changes setup currents for the X-direction scanning electromagnet 32 and the Y-direction scanning electromagnet 33 on the basis of control inputs (commands) outputted from the irradiation management device 38 for the X-direction scanning electromagnet 32 and the Y-direction scanning electromagnet 33.

Here, the scanning irradiation method of the particle beam irradiation apparatus 58 will be described as being a hybrid-scanning irradiation method (a method in which the beam is not stopped when the beam irradiation position (spot) is changed), specifically, as being such a method in which, as is done by a raster-scanning irradiation method, the charged particle beam 31 is not stopped when the irradiation position of the charged particle beam 31 is changed, and in which, as in a spot-scanning irradiation method, the beam irradiation position moves between spot positions successively. The spot counter 43 serves to measure an irradiation dose during when the beam irradiation position of the charged particle beam 31 is staying. The inter-spot counter 44 serves to measure an irradiation dose during when the beam irradiation position of the charged particle beam 31 is moving. The trigger generation unit 42 serves to generate a dose completion signal when the dose of the charged particle beam 31 at a beam irradiation position reaches the target irradiation dose.

Figure 3:
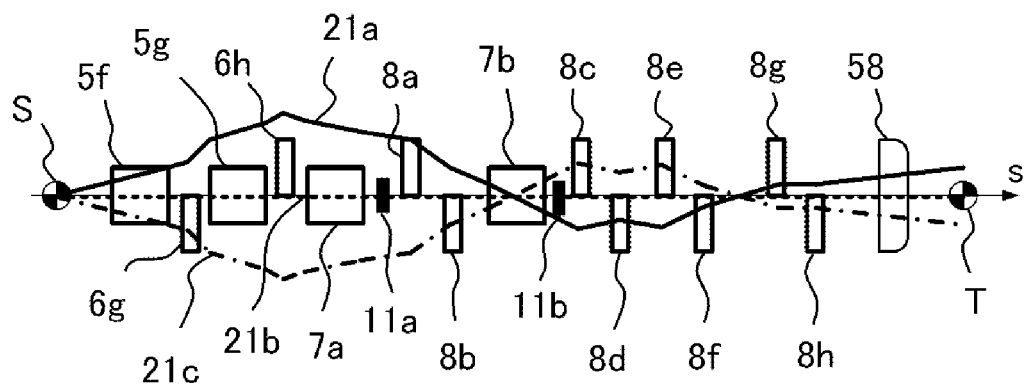
FIG. 3 is a diagram showing beam trajectories before correction in a beam transport system according to Embodiment 1 of the invention.
Figure 5:
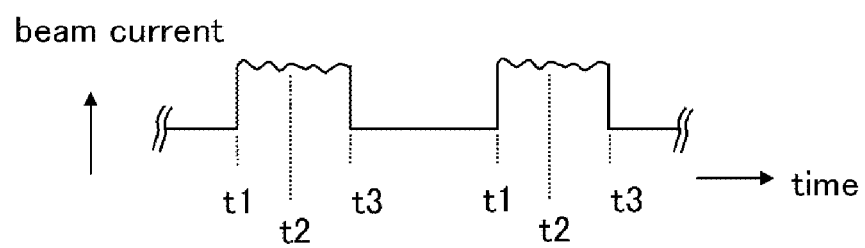
FIG. 5 is a diagram illustrating a current for a beam emitted to the beam transport system according to Embodiment 1 of the invention.
Figure 6:
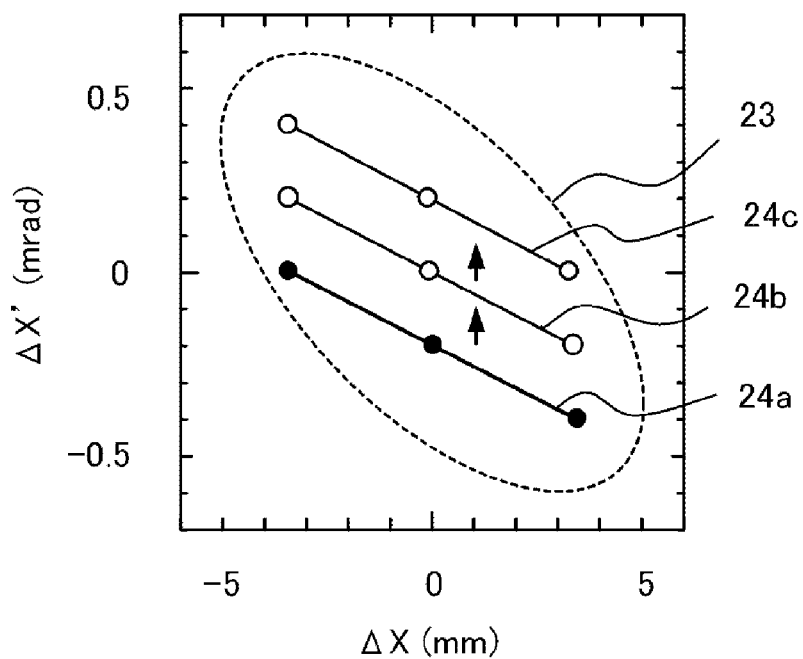
FIG. 6 is a graph showing phase spatial distributions at a start point of the beam transport system according to Embodiment 1 of the invention.

The beam transport system 4 for the case where the charged particle beam 31 is subjected to beam emission from the accelerator 3 by an RF sweep method, will be shown. In the injection system 1, the accelerator (synchrotron) 3 and the beam transport system 4 of the particle beam therapy system 20 in FIG. 1, an optical system in which the chromatic aberration at the irradiation position T is nearly nullified (no movement of the beam) is established by Steps described later. FIG. 3 is a diagram showing beam trajectories before correction in the beam transport system according to Embodiment 1 of the invention. In FIG. 3, a portion from the start point S to the terminal point (irradiation position) T for designing the optical system of the beam transport system 4, is shown in a linear fashion. In FIG. 3, the abscissa represents the s-axis that is an axis in the traveling direction of the charged particle beam 31, and the ordinate represents a distance $\Delta X$ in the x-direction. FIG. 5 is a diagram illustrating a current for the beam emitted to the beam transport system according to Embodiment 1 of the invention. FIG. 6 is a graph showing phase spatial distributions at the start point of the beam transport system according to Embodiment 1 of the invention. In FIG. 6, the abscissa represents the distance $\Delta X$ in the x-direction perpendicular to the central axis of the beam trajectories, and the ordinate represents an inclination $\Delta X'$ at $\Delta X$ relative to the central axis of the beam trajectories.

As described previously, as to the actual charged particle beam 31, its current value intermittently goes back and forth between zero and a value other than zero, so that the phase spatial distribution of the charged particle beam 31 differs among at Times t1, t2 and t3. For example, a phase spatial distribution 23 of the charged particle beam 31 is: a phase spatial distribution 24a at Time t1 (at the beginning of the spill); a phase spatial distribution 24b at Time t2 (at the middle of the spill); and a phase spatial distribution 24c at Time t3 (at the end of the spill). A beam trajectory 21a in FIG. 3 is a beam trajectory at Time t1 (at the beginning of the spill) and is a beam trajectory corresponding to the phase spatial distribution 24a. A beam trajectory 21b is a beam trajectory at Time t2 (at the middle of the spill) and is a beam trajectory corresponding to the phase spatial distribution 24b. A beam trajectory 21c is a beam trajectory at Time t3 (at the end of the spill) and is a beam trajectory corresponding to the phase spatial distribution 24c.

In Step S1, optical parameters when the synchrotron (accelerator 3) is in an ideal state are calculated by the optical parameter calculator 17. The optical parameters are outputted to the device controller 16, and then the device controller 16 calculates current values for the respective electromagnets on the basis of the optical parameters, and sends the current values to the electromagnet power source 15. The electromagnet power source sets a current for each of the electromagnets (bending electromagnet 7, quadrupole electromagnet 8) in the beam transport system 4. Note that the electromagnet power source 15 also sets a current for each of the electromagnets (bending electromagnet 5, quadrupole electromagnet 6) in the injection system 1 and the accelerator 3.

In Step S2, commands matched to the optical parameters for the accelerator 3 are sent by the device controller 16 to the RF-acceleration power source 12 and the electromagnet power source 15, so that the respective devices (bending electromagnets 5, quadrupole electromagnets 6, acceleration cavity 9) are operated according to these commands to thereby accelerate and emit the charged particle beam 31. Note that, here, because of the RF sweep method, at the time of emission, the RF frequency of the RF-acceleration power source 12 is swept adequately, but the RF-kick power source 13 is not operated. In FIG. 1, although the x-direction kick electrode 10 and the RF-kick power source 13 are illustrated, they are not used in the RF sweep method and thus may be omitted from the accelerator 3.

In Step S3, as to the charged particle beam 31 emitted from the accelerator 3, its profile data in each time period is acquired by the beam profile monitors 11a, 11b, and the beam position is analyzed by the beam analyzer 14. The time period for acquiring the profile data is a time period from the beginning of emission to the end of emission, and corresponds to the time period from Time t1 to Time t3 in FIG. 5.

In Step S4, momentum dispersion functions ηa and ηb represented by a formula (1) and a formula (2) are calculated from position-variation information in the profile data, where p denotes a momentum, Δp denotes a momentum difference relative to a momentum at Time t0 that is given as a reference, and Δx denotes a positional difference relative to a position in the x-direction at Time t0 that is given as a reference. Note that the suffix "a" is indicative of a value at the beam profile monitor 11a and the suffix "b" is indicative of a value at the beam profile monitor 11b.

[Mathematical 1]

$$\Delta x_a = \eta_a \cdot \Delta p/p$$

$$\Delta x_a' = \eta_a' \cdot \Delta p/p \quad (1)$$

[Mathematical 2]

$$\Delta x_b = \eta_b \cdot \Delta p/p$$

$$\Delta x_b' = \eta_b' \cdot \Delta p/p \quad (2)$$

In Step S5, momentum dispersion functions (ηx, ηx'), (ηy, ηy') at the start point S and the optical parameters are calculated and outputted to the device controller 16. Momentum dispersion functions at the beam profile monitors 11a, 11b are represented by a formula (3) and a formula (4), respectively. Note that the suffix "i" in the right side is indicative of an input, namely, indicative of the start point S. In the formula (3) and the formula (4), Ma and Mb are beam transfer matrices from the start point S to the beam profile monitors 11a, 11b, which are represented by a formula (5) and a formula (6).

[Mathematical 3]

$$\begin{pmatrix} \eta_x \\ \eta_x' \\ 1 \end{pmatrix}_a = M_a \begin{pmatrix} \eta_x \\ \eta_x' \\ 1 \end{pmatrix}_i \quad (3)$$

[Mathematical 4]

$$\begin{pmatrix} \eta_x \\ \eta_x' \\ 1 \end{pmatrix}_b = M_b \begin{pmatrix} \eta_x \\ \eta_x' \\ 1 \end{pmatrix}_i \quad (4)$$

[Mathematical 5]

$$M_a = \begin{pmatrix} m_{11} & m_{12} & m_{13} \\ m_{21} & m_{22} & m_{23} \\ 0 & 0 & 1 \end{pmatrix}_a \quad (5)$$

[Mathematical 6]

$$M_b = \begin{pmatrix} m_{11} & m_{12} & m_{13} \\ m_{21} & m_{22} & m_{23} \\ 0 & 0 & 1 \end{pmatrix}_b \quad (6)$$

In the optical parameter calculator 17, the momentum dispersion functions (ηx, ηx'), (ηy, ηy') at the start point S are calculated from the formula (3) and the formula (4). For example, such momentum dispersion functions (ηx, ηx'), (ηy, ηy') that afford the phase spatial distributions 23 in FIG. 6 are calculated. The parameters by which the momentum dispersion functions at the irradiation position as the terminal point T become (0, 0)—(Condition 1), are calculated from a formula (7) and outputted to the device controller 16. This Condition 1 is a beginning condition at the irradiation position (terminal point T) at the time the profile data is detected by the beam profile monitors 11.

[Mathematical 7]

$$\begin{pmatrix} 0 \\ 0 \\ 1 \end{pmatrix}_f = M_f \begin{pmatrix} \eta_x \\ \eta_x' \\ 1 \end{pmatrix}_i \quad (7)$$

In Step S6, for the second time, the device controller 16 sends the current values based on the optical parameters that afford Condition 1, to the electromagnet power source 15, to thereby set a specified current for each of the electromagnets.

Figure 4:
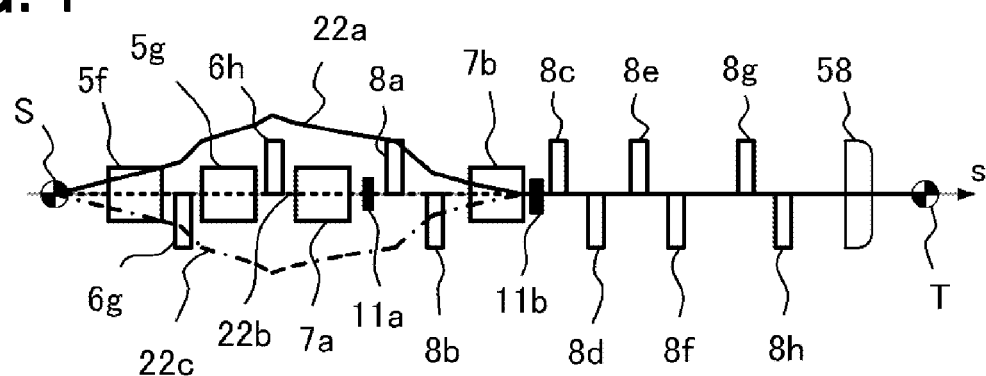
FIG. 4 is a diagram showing beam trajectories after correction in the beam transport system according to Embodiment 1 of the invention.
Figure 7:
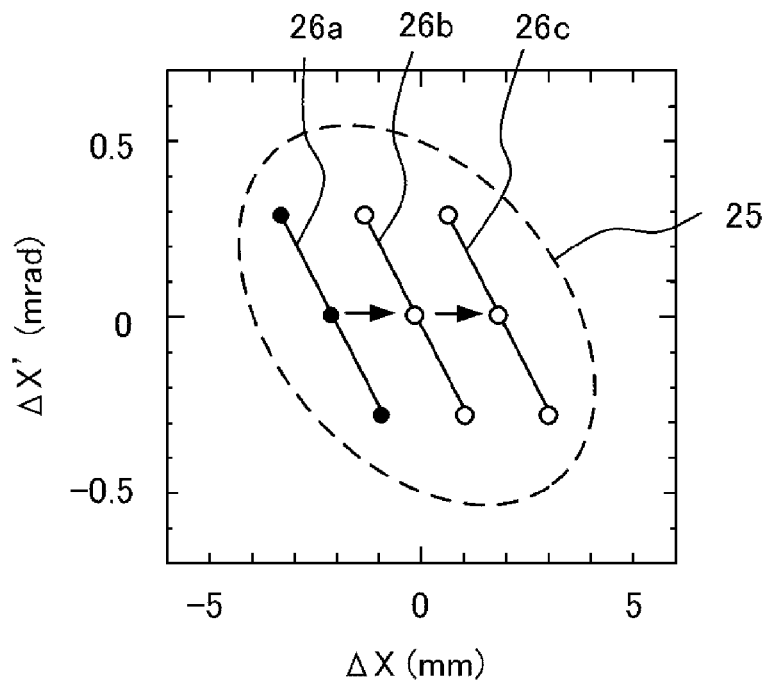
FIG. 7 is a graph showing phase spatial distributions before correction at a terminal point of the beam transport system according to Embodiment 1 of the invention.
Figure 8:
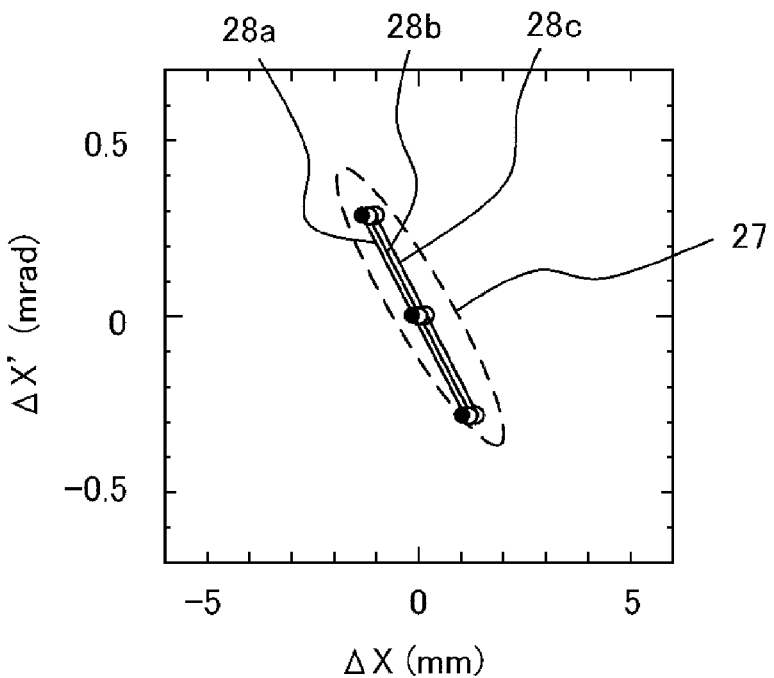
FIG. 8 is a graph showing phase spatial distributions after correction at the terminal point of the beam transport system according to Embodiment 1 of the invention.
Figure 9:
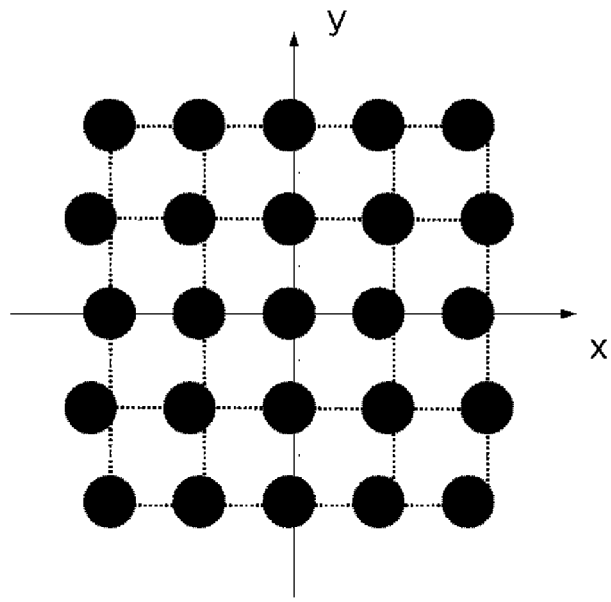
FIG. 9 is a graph showing beam-spot positions before correction at the terminal point of the beam transport system according to Embodiment 1 of the invention.
Figure 10:
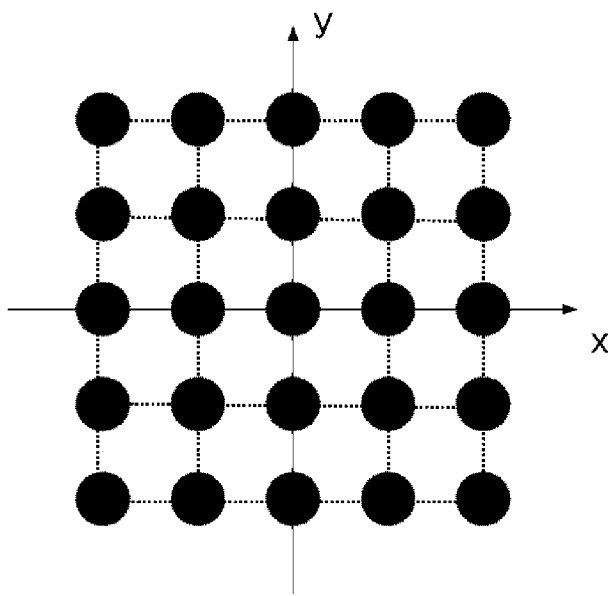
FIG. 10 is a graph showing beam-spot positions after correction at the terminal point of the beam transport system according to Embodiment 1 of the invention.

When the respective electromagnets are set to the current values in Step S6, the beam causes no movement at the irradiation position (terminal point T) as shown in FIG. 4, FIG. 9 and FIG. 10, so that the chromatic aberration is nearly nullified (substantially zero) as shown in FIG. 7 and FIG. 8. FIG. 4 is a diagram showing beam trajectories after correction in the beam transport system according to Embodiment 1 of the invention. FIG. 7 is a graph showing phase spatial distributions before correction at the terminal point of the beam transport system according to Embodiment 1 of the invention, and FIG. 8 is a graph showing phase spatial distributions after correction at the terminal point of the beam transport system according to Embodiment 1 of the invention. FIG. 9 is a graph showing beam-spot positions before correction at the terminal point of the beam transport system according to Embodiment 1 of the invention, and FIG. 10 is a graph showing beam-spot positions after correction at the terminal point of the beam transport system according to Embodiment 1 of the invention.

The beam trajectory 22a in FIG. 4 is a beam trajectory after correction at Time t1 (at the beginning of the spill), that is a beam trajectory resulted from correcting the beam trajectory 21a in FIG. 3. The beam trajectory 22b is a beam trajectory after correction at Time t2 (at the middle of the spill), that is a beam trajectory resulted from correcting the beam trajectory 21b in FIG. 3. The beam trajectory 22c is a beam trajectory after correction at Time t3 (at the end of the spill), that is a beam trajectory resulted from correcting the beam trajectory 21c in FIG. 3. Note that the beam trajectory 22b in FIG. 4 is placed on the s-axis also after correction like the beam trajectory 21b in FIG. 3.

In FIG. 7 and FIG. 8, the abscissa represents the distance ΔX in the x-direction perpendicular to the central axis of the beam trajectories, and the ordinate represents the inclination ΔX' at ΔX relative to the central axis of the beam trajectories. In FIG. 9 and FIG. 10, the abscissa represents the aforementioned x-axis in the beam coordinate system, and the ordinate represents the y-axis in the beam coordinate system. As shown in FIG. 7, the phase spatial distributions before correction at the terminal point T of the beam transport system 4 are phase spatial distributions 25, in which a phase spatial distribution 26a is provided at Time t1 (at the beginning of the spill), a phase spatial distribution 26b is provided at Time t2 (at the middle of the spill), and a phase spatial distribution 26c is provided at Time t3 (at the end of the spill). As shown in FIG. 8, the phase spatial distributions after correction at the terminal point T of the beam transport system 4 are phase spatial distributions 27, in which a phase spatial distribution 28a is provided at Time t1 (at the beginning of the spill), a phase spatial distribution 28b is provided at Time t2 (at the middle of the spill), and a phase spatial distribution 28c is provided at Time t3 (at the end of the spill). In FIG. 8, for the sake of easy understanding, the phase spatial distributions 28a, 28b, 28c are illustrated as being somewhat displaced from each other; however, the chromatic aberration is nearly nullified (substantially zero). When the chromatic aberration is nearly nullified (substantially zero), the beam position on the phase space is stable regardless of time. As thus described, at the terminal point T of the beam transport system 4 of Embodiment 1, the chromatic aberration due to the phase spatial distributions 25 before correction is large, whereas the chromatic aberration due to the phase spatial distributions 27 after correction is nearly nullified (substantially zero).

In the phase spatial distributions 25 before correction, $\Delta X$ is from −4.2 mm to 4.1 mm, whereas, in the phase spatial distributions 27 after correction, $\Delta X$ is from −2.0 mm to 2.0 mm. As shown in FIG. 3, before correction, a variation in beam trajectory occurs at the terminal point T, so that the beam size is enlarged so as to depart from its planned value. Note that, even though the beam size is different to the value of a width from the lower limit to the upper limit of $\Delta X$ in the phase distributions, the beam size becomes larger as the value of the width of $\Delta X$ becomes larger. As shown in FIG. 4, with respect to the beam trajectories after correction, the beam trajectories 22a, 22b, 22c are all placed on the s-axis after the installation position of the beam profile monitor 11b. Because of no variation in beam trajectory after correction at the terminal point T, the beam size at the terminal point T is a beam size as planned, namely, the beam size at the terminal point T is not enlarged so as to depart from the planned value.

Using FIG. 9 and FIG. 10, description will be made about spot positions in scanning irradiation and a dose distribution in uniform irradiation. In order to make a spot-position displacement of the charged particle beam 31 easily viewable, a broken line grid is added in FIG. 9 and in FIG. 10. Each corner in the broken line grid corresponds to a planned spot position. As shown in FIG. 9, in the case before correction and with a chromatic aberration in the x-direction, a gravity center of the beam having a spread (center of each circle in FIG. 9 and FIG. 10) is positionally displaced in the x-direction. In contrast, as shown in FIG. 10, in the case after correction and without a chromatic aberration in the x-direction, the gravity center of the beam having a spread is matched to each of the corners of the broken line grid, so that the positions in the x-direction are matched to those as planned. When the spot positions are displaced from those in the plan, even if going to achieve radiation that provides a uniform irradiation, because of a difference in irradiation dose for each irradiation spot from a planned dose, unevenness occurs in the actual dose distribution. The beam transport system 4 of Embodiment 1 can nearly nullify (set to substantially zero) the chromatic aberration at the terminal point T, so that the spot positions in scanning irradiation can be matched to those as planned.

The beam transport system 4 of Embodiment 1 can nearly nullify the chromatic aberration of the charged particle beam 31 at an irradiation position (terminal point T) at the time of no operation of the particle beam irradiation apparatus 58, namely, at the isocenter, so that the spot positions in scanning irradiation can be matched to those as planned. Although the charged particle beam 31 is scanned in the particle beam irradiation apparatus 58 so as to form a broad irradiation field, a highly accurate particle beam therapy can be achieved when, even if the chromatic aberration of the beam is not nullified at an irradiation position under scanning, the irradiation position of the beam falls in an allowable range. Thus, the chromatic aberration may be that which is not zero but with which the irradiation position falls in the allowable range. Accordingly, the beam transport system 4 of Embodiment 1 designed as described above can nearly nullify (set to substantially zero) the chromatic aberration of the beam at the irradiation position of the charged particle beam 31, so that the spot positions in scanning irradiation can be highly accurately matched to those as planned.

Even in the case with a small-sized synchrotron, and even when the chromatic aberration is not nullified at the start point S in the optical parameter design of the beam transport system 4 using a high-performance bending electromagnet, quadrupole electromagnet or six-pole electromagnet, the beam transport system 4 of Embodiment 1 can nearly nullify (set to substantially zero) the chromatic aberration of the beam at the irradiation position of the charged particle beam 31. Accordingly, the beam transport system 4 of Embodiment 1, even in the case with a small-sized synchrotron, can avoid bringing enlargement or complexity of the accelerator or the beam transport system, to thereby suppress the accelerator and the beam transport system from becoming significantly expensive.

The design methodology of the beam transport system 4 shown in Embodiment 1 is such that in the beam transport system being set to an ideal magnetic field condition, beam positions in the middle of the beam transport system 4 are measured using the profile data detected by the beam profile monitors 11, and the beam temporal-variation related amounts that are beam-position temporal variation amounts at the beam profile monitors 11 are calculated, so that the x-direction momentum dispersion functions $\eta x$, $\eta x'$ and the y-direction momentum dispersion functions $\eta y$, $\eta y'$ that are a part of the initial condition at the beam communication point (start point S), are calculated as the start-point momentum dispersion functions; and new optical parameters for the beam transport system 4 are set using, as the initial condition, the above Condition 1 that is the beginning condition at the irradiation position (terminal point T) at the time of detecting the profile data, and the start-point momentum dispersion functions. When this design methodology is applied, the adjustment becomes easy even at the installation site. Thus, as differed from a method in which an adjustment has to be made many times like a conventional case, it is possible to reduce the time for the adjustment of the beam transport system in comparison to the conventional case.

Description will be made about the number of the bending electromagnets 7 and the quadrupole electromagnets 8 in the beam transport system 4. In the case where the charged particle beam 31 is caused not to move in the x-direction at the irradiation position (terminal point T), one or more bending electromagnets 7 for causing deflection in the x-direction is placed and two or more quadrupole electromagnets 8 for controlling focusing/defocusing in the x-direction are placed upstream of that bending electromagnet 7. In FIG. 3 and FIG. 4, the bending electromagnet 7b and the quadrupole electromagnets 8a, 8b are the requisite minimum ones among the bending electromagnets 7 and the quadrupole electromagnets 8. Meanwhile, in the case where the charged particle beam 31 is caused not to move in the y-direction at the irradiation position (terminal point T), one or more bending electromagnets 7 for causing deflection in the y-direction is placed and two or more quadrupole electromagnets 8 for controlling focusing/defocusing in the y-direction are placed upstream of that bending electromagnet 7.

In FIG. 1, FIG. 3 and FIG. 4, although the bending electromagnet 7 for causing deflection in the y-direction is not illustrated in the beam transport system 4, it suffices that: it is placed, for example, at the downstream side of the bending electromagnet 7b; and two of the quadrupole electromagnets 8 placed upstream of the bending electromagnet 7 for causing deflection in the y-direction are each set to serve as a quadrupole electromagnet for controlling focusing/defocusing in the y-direction. In the example of FIG. 1, the circulating charged particle beam 31 is Introduced into the beam transport system 4 by being moved in the x-direction, so that a y-direction chromatic aberration at the start point S can be made sufficiently small by the bending electromagnets 5 and the quadrupole electromagnets 6 placed in the accelerator 3. Thus, with respect to the y-direction bending electromagnet 7 and quadrupole electromagnets 8 for causing the charged particle beam 31 not to move in the y-direction at the irradiation position (terminal point T), they just have to be placed when the y-direction chromatic aberration at the start point S is large.

As described above, according to the beam transport system 4 of Embodiment 1, it comprises; at least one bending electromagnet 7 that deflects the charged particle beam 31; at least two quadrupole electromagnets 8 that focus or defocus the charged particle beam 31; at least one beam profile monitor 11 that detects profile data of the charged particle beam 31; the beam analyzer 14 that calculates based on the profile data, the beam temporal-variation related amount that is a beam-position temporal variation amount or a beam diameter at the beam profile monitor 11; the optical parameter calculator 17 that calculates optical parameters of the beam transport system 4; and the electromagnet power source 15 that sets an excitation current of each of the bending electromagnet 7 and the quadrupole electromagnets 8, based on the optical parameters calculated by the optical parameter calculator 17. The optical parameter calculator 17 of the beam transport system 4 of Embodiment 1 is characterized in that: it calculates based on the beam temporal-variation related amount, the start-point momentum dispersion function that is a momentum dispersion function η, η' of the charged particle beam 31 at a start point in design (start point S) of the beam transport system 4 being set on the beam trajectory of the accelerator 3; and it calculates said optical parameters using, as an initial condition, the start-point momentum dispersion function and a beginning condition at the irradiation position (terminal point T) at the time of detecting the profile data. Thus, even in the case of the beam emitted from a small-sized synchrotron, it is possible to nearly nullify the chromatic aberration of the beam at the beam irradiation position (terminal point T).

According to the particle beam therapy system 20 of Embodiment 1, it comprises: the accelerator 3 that accelerates the charged particle beam 31; the beam transport system 4 that transports the charged particle beam 31 emitted from the accelerator 3 to the irradiation position (terminal point T); and the particle beam irradiation apparatus 58 that is placed at a downstream side of the beam transport system 4 and that radiates the charged particle beam 31 to the irradiation target 45 so as to form an intended irradiation field. According to the particle beam therapy system 20 of Embodiment 1, the beam transport system 4 comprises; at least one bending electromagnet 7 that deflects the charged particle beam 31; at least two quadrupole electromagnets 8 that focus or defocus the charged particle beam 31; at least one beam profile monitor 11 that detects profile data of the charged particle beam 31; the beam analyzer 14 that calculates based on the profile data, the beam temporal-variation related amount that is a beam-position temporal variation amount or a beam diameter at the beam profile monitor 11; the optical parameter calculator 17 that calculates optical parameters of the beam transport system 4; and the electromagnet power source 15 that sets an excitation current of each of the bending electromagnet 7 and the quadrupole electromagnets 8, based on the optical parameters calculated by the optical parameter calculator 17. According to the particle beam therapy system 20 of Embodiment 1, the optical parameter calculator 17 is characterized in that: it calculates based on the beam temporal-variation related amount, the start-point momentum dispersion function that is a momentum dispersion function η, η' of the charged particle beam 31 at a start point in design (start point S) of the beam transport system 4 being set on the beam trajectory of the accelerator 3; and it calculates said optical parameters using, as an initial condition, the start-point momentum dispersion function and a beginning condition at the irradiation position (terminal point T) at the time of detecting the profile data. Thus, even in the case of the beam emitted from a small-sized synchrotron, it is possible to nearly nullify the chromatic aberration of the beam at the beam irradiation position (terminal point T), to thereby control the beam irradiation position (terminal point T) highly accurately.

Embodiment 2

Figure 11:
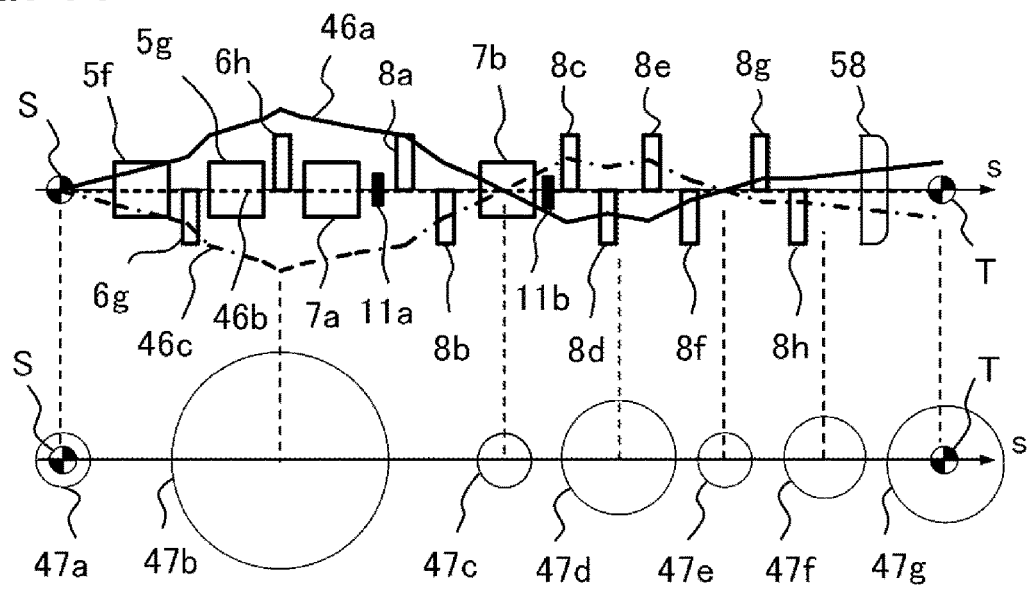
FIG. 11 is a diagram showing beam trajectories and beam diameters before correction in a beam transport system according to Embodiment 2 of the invention.

In Embodiment 1, description has been made about the beam transport system 4 for the case where the charged particle beam 31 is subjected to beam emission from the accelerator 3 by an RF sweep method. In Embodiment 2, description will be made about the beam transport system 4 for the case where the charged particle beam 31 is subjected to beam emission from the accelerator 3 by an RF knockout method. In the injection system 1, the accelerator (synchrotron) 3 and the beam transport system 4 of the particle beam therapy system 20 in FIG. 1, an optical system in which, at the irradiation position T, the chromatic aberration is nearly nullified (no movement of the beam) and the beam diameter is not enlarged, is established by Steps described later. The RE knockout method is an emission method in which, at the emission point of the synchrotron, particles having a variety of energies are mixed together at a given time. For this reason, the RF knockout method results in the beam being transported under a situation where the momentum dispersion functions (ηx, ηx'), (ηy, ηy') and the twiss parameters (αx, βx), (αy, βy) at the start point S for designing the optical system in the beam transport system 4 are unknown. Accordingly, due to a chromatic aberration, the beam diameter is observed to be large at the irradiation position (terminal point T) as shown in FIG. 11. When this is corrected by the design methodology of Embodiment 2, it is possible to achieve a small-diameter beam at the irradiation position (terminal point T) as shown in FIG. 12.

Figure 12:
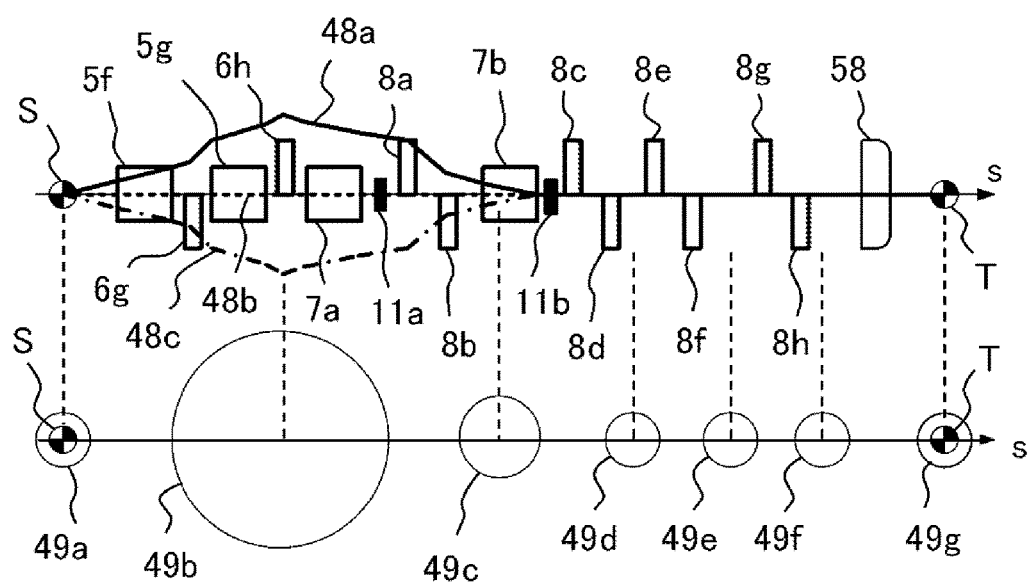
FIG. 12 is a diagram showing beam trajectories and beam diameters after correction in the beam transport system according to Embodiment 2 of the invention.

FIG. 11 is a diagram showing beam trajectories and beam diameters before correction in the beam transport system according to Embodiment 2 of the invention, and FIG. 12 is a diagram showing beam trajectories and beam diameters after correction in the beam transport system according to Embodiment 2 of the invention. At the upper side each in FIG. 11 and FIG. 12, a portion from the start point S to the terminal point (irradiation position) T for designing the optical system of the beam transport system 4, is shown in a linear fashion. At the lower side each in FIG. 11 and FIG. 12, the beam diameters with respect to positions being on the s-axis and indicated by broken lines drawn from the upper side, are schematically shown by circles. A beam trajectory 46a in FIG. 11 corresponds to a beam trajectory when Δp/p>0 is given in the formula (1) and the formula (2). A beam trajectory 46b in FIG. 11 corresponds to a beam trajectory when Δp/p=0 is given in the formula (1) and the formula (2), and a beam trajectory 46c in FIG. 11 corresponds to a beam trajectory when Δp/p<0 is given in the formula (1) and the formula (2). The beam diameter at the start point S is a diameter of the circle indicated by numeral 47a, and the beam diameter at the terminal point T is a diameter of the circle indicated by numeral 47g. Between the start point S and the terminal point T, there are shown five beam diameters as diameters of the circles indicated by numerals 47b, 47c, 47d, 47e and 47f.

Like in FIG. 11, a beam trajectory 48a in FIG. 12 corresponds to a beam trajectory when Δp/p>0 is given in the formula (1) and the formula (2). A beam trajectory 48b in FIG. 12 corresponds to a beam trajectory when Δp/p=0 is given in the formula (1) and the formula (2), and a beam trajectory 48c in FIG. 12 corresponds to a beam trajectory when Δp/p<0 is given in the formula (1) and the formula (2). The beam diameter at the start point S is a diameter of the circle indicated by numeral 49a, and the beam diameter at the terminal point T is a diameter of the circle indicated by numeral 49g. Between the start point S and the terminal point T, there are shown five beam diameters as diameters of the circles indicated by numerals 49b, 49c, 49d, 49e and 49f.

In Step S11, optical parameters when the synchrotron (accelerator 3) is in an ideal state are calculated by the optical parameter calculator 17. The optical parameters are outputted to the device controller 16, and then the device controller 16 calculates current values for the respective electromagnets on the basis of the optical parameters, and sends the current values to the electromagnet power source 15. The electromagnet power source sets a current for each of the electromagnets (bending electromagnet 7, quadrupole electromagnet 8) in the beam transport system 4. Note that the electromagnet power source 15 also sets a current for each of the electromagnets (bending electromagnet 5, quadrupole electromagnet 6) in the injection system 1 and the accelerator 3.

In Step S12, commands matched to the optical parameters for the accelerator 3 are sent by the device controller 16 to the RF-acceleration power source 12 and the electromagnet power source 15, so that the respective devices (bending electromagnets 5, quadrupole electromagnets 6, acceleration cavity 9, x-direction kick electrode 10) are operated according to these commands to thereby accelerate and emit the charged particle beam 31. Note that, here, because of the RF knockout method, at the time of emission, the RF frequency of the RF-acceleration power source 12 is not changed, but the RE kick electrode 13 is operated so as to increase an emittance in the lateral direction (x-direction) to thereby emit the charged particle beam 31. Note that the emittance corresponds to an area on the phase space of the beam.

In Step S13, as to the charged particle beam 31 emitted from the accelerator 3, its profile data in each time period is acquired by the beam profile monitors 11a, 11b, and the beam diameter is analyzed by the beam analyzer 14. The time period for acquiring the profile data is a time period from the beginning of emission to the end of emission, and corresponds to the time period from Time t1 to Time t3 in FIG. 5. In the RF knockout method, portions of the charged particle beam 31 having momentums in a given range are emitted simultaneously from the accelerator 3. Thus, the beam diameter is calculated using a formula (11), a formula (12) and a formula (13).

In general, when a beam is transported with a transfer matrix M that is represented by the matrix of the formula (11), twiss parameters α, β, γ of the beam are transferred as shown in the formula (12). Further, a beam diameter r at a transported position is represented by the formula (13). The twiss parameters α, β, γ in the right side of the formula (12) are those before transfer with the transfer matrix M, and the twiss parameters α, β, γ in the left side of the formula (12) are those after transfer with the transfer matrix M. The respective members in a transfer matrix $M_t$ for the twiss parameters in the formula (12) are written using the members of $m_{11}$, $m_{12}$, $m_{13}$, $m_{21}$, $m_{22}$ and $m_{23}$ in the transfer matrix M of the formula (11). In the formula (13), $r_x$ denotes a beam diameter in the x-direction, $\epsilon_x$ denotes an emittance in the x-direction, $\beta_x$ denotes a twiss parameter β in the x-direction, and $\eta_x$ denotes a momentum dispersion function in the x-direction.

[Mathematical 8]

$$M = \begin{pmatrix} m_{11} & m_{12} & m_{13} \\ m_{21} & m_{22} & m_{23} \\ 0 & 0 & 1 \end{pmatrix} \quad (11)$$

[Mathematical 9]

$$\begin{pmatrix} \beta \\ \alpha \\ \gamma \end{pmatrix} = \begin{pmatrix} m_{11}^2 & -2m_{11}m_{12} & m_{12}^2 \\ -m_{21}m_{11} & 1+2m_{12}m_{21} & -m_{12}m_{22} \\ m_{21}^2 & -2m_{22}m_{21} & m_{22}^2 \end{pmatrix} \begin{pmatrix} \beta \\ \alpha \\ \gamma \end{pmatrix} \quad (12)$$

[Mathematical 10]

$$r_x = \sqrt{\varepsilon_x \beta_x} + \eta_x \cdot \Delta p/p \quad (13)$$

In Step S14, optical formulae of the charged particles at the beam profile monitors 11a, 11b are calculated. The optical formulae of the charged particles at the beam profile monitor 11a are represented by a formula (14), a formula (17) and a formula (20). The optical formulae of the charged particles at the beam profile monitor 11b are represented by a formula (23), a formula (26) and a formula (29). First of all, description will be made about the optical formulae of the charged particles at the beam profile monitor 11a. Note that the suffix "i" in the formulae shown below is indicative of an input, namely, indicative of the start point S. In the formulae shown below, the suffix "a" is indicative of a value at the beam profile monitor 11a, and the suffix "b" is indicative of a value at the beam profile monitor 11b. The suffix "x" is indicative that the corresponding variable is a value in the x-direction.

[Mathematical 11]

$$\begin{pmatrix} \beta_x \\ \alpha_x \\ \gamma_x \end{pmatrix}_a = \begin{pmatrix} m_{11}^2 & -2m_{11}m_{12} & m_{12}^2 \\ -m_{21}m_{11} & 1+2m_{12}m_{21} & -m_{12}m_{22} \\ m_{21}^2 & -2m_{22}m_{21} & m_{22}^2 \end{pmatrix}_a \begin{pmatrix} \beta_x \\ \alpha_x \\ \gamma_x \end{pmatrix}_i \quad (14)$$

The formula (14) shows that x-direction twiss parameters $\alpha_x$, $\beta_x$, $\gamma_x$ at the start point S are transferred respectively as $\alpha_{xa}$, $\beta_{xa}$, $\gamma_{xa}$ using a transfer matrix $M_{ta}$ for the twiss parameters. The transfer matrix $M_{ta}$ for the twiss parameters is the matrix in the formula (14) to which the suffix "a" is attached. When transfer matrices $M_{a1}$, $M_{a2}$ in the case where excitations of the quadrupole electromagnet 6 and the quadrupole electromagnet 8 are changed are used, namely, when transfer matrices $M_{ta1}$, $M_{ta2}$ for the twiss parameters are used, the x-direction twiss parameters $\alpha_x$, $\beta_x$, $\gamma_x$ are transferred as shown in a formula (15) and a formula (16). The transfer matrices $M_{ta1}$, $M_{ta2}$ are provided in a form similar to that of the transfer matrix $M_{ta}$. Note that the suffix "a1" is indicative of a value at the beam profile monitor 11a in the case where the parameters are transferred using the transfer matrix $M_{a1}$ or the transfer matrix $M_{ta1}$, and the suffix "a2" is indicative of a value at the beam profile monitor 11a in the case where the parameters are transferred using the transfer matrix $M_{a2}$ or the transfer matrix $M_{ta2}$.

[Mathematical 12]

$$\begin{pmatrix} \beta_x \\ \alpha_x \\ \gamma_x \end{pmatrix}_{a1} = M_{ta1} \begin{pmatrix} \beta_x \\ \alpha_x \\ \gamma_x \end{pmatrix}_i \quad (15)$$

[Mathematical 13]

$$\begin{pmatrix} \beta_x \\ \alpha_x \\ \gamma_x \end{pmatrix}_{a2} = M_{ta2} \begin{pmatrix} \beta_x \\ \alpha_x \\ \gamma_x \end{pmatrix}_i \quad (16)$$

When the transfer matrix at the beam profile monitor lie has respective members similar to those in the formula (11), the twiss parameters $\alpha$, $\beta$, $\gamma$ of the beam are transferred as shown in the formula (14). An x-direction beam diameter $r_{xa}$ at the beam profile monitor 11a is represented by a formula (17). $\beta_{xa}$ denotes an x-direction twiss parameter $\beta$ at the beam profile monitor 11a, and $\eta_{xa}$ denotes an x-direction momentum dispersion function at the beam profile monitor 11a. As shown in a formula (20), the x-direction momentum dispersion function $\eta_{xa}$ is obtained from the x-direction momentum dispersion function $\eta_x$ at the start point S after being transferred using the transfer matrix $M_a$ to become $\eta_{xa}$.

[Mathematical 14]

$$r_{xa} = \sqrt{\epsilon_x \beta_{xa}} + \eta_{xa} \cdot \Delta p/p \quad (17)$$

When the transfer matrix $M_{a1}$ in the case where excitations of the quadrupole electromagnet 6 and the quadrupole electromagnet 8 are changed is used, an x-direction beam diameter $r_{xa1}$ at the beam profile monitor 11e is represented by a formula (18), like the case of the formula (17). Meanwhile, when the transfer matrix $M_{a2}$ in the case where excitations of the quadrupole electromagnet 6 and the quadrupole electromagnet 8 are changed is used, an x-direction beam diameter $r_{xa2}$ at the beam profile monitor 11a is represented by a formula (19), like the case of the formula (17). $\beta_{xa1}$ denotes an x-direction twiss parameter $\beta$ at the beam profile monitor 11a having been transferred using the transfer matrix $M_{ta1}$, and $\eta_{xa1}$ denotes an x-direction momentum dispersion function at the beam profile monitor 11a having been transferred using the transfer matrix $M_{a1}$. $\beta_{xa2}$ denotes an x-direction twiss parameter $\beta$ at the beam profile monitor 11a having been transferred using the transfer matrix $M_{ta2}$, and $\eta_{xa2}$ denotes an x-direction momentum dispersion function at the beam profile monitor 11a having been transferred using the transfer matrix $M_{a2}$.

[Mathematical 15]

$$r_{xa1} = \sqrt{\epsilon_x \beta_{xa1}} + \eta_{xa1} \cdot \Delta p/p \quad (18)$$

[Mathematical 16]

$$r_{xa2} = \sqrt{\epsilon_x \beta_{xa2}} + \eta_{xa2} \cdot \Delta p/p \quad (19)$$

The formula (20) shows that the x-direction momentum dispersion function $\eta_x$ at the start point S, and $\eta_x'$ given as its inclination relative to the s-direction, are transferred respectively to become $\eta_{xa}$ and $\eta_{xa}'$ using the transfer matrix $M_a$. When the transfer matrices $M_{a1}$, $M_{a2}$ in the case where excitations of the quadrupole electromagnet 6 and the quadrupole electromagnet 8 are changed are used, the x-direction momentum dispersion function $\eta_x$ and the inclination $\eta_x'$ relative to the s-direction, are transferred as shown in a formula (21) and a formula (22).

[Mathematical 17]

$$\begin{pmatrix} \eta_x \\ \eta_x' \\ 1 \end{pmatrix}_a = M_a \begin{pmatrix} \eta_x \\ \eta_x' \\ 1 \end{pmatrix}_i \quad (20)$$

[Mathematical 18]

$$\begin{pmatrix} \eta_x \\ \eta_x' \\ 1 \end{pmatrix}_{a1} = M_{a1} \begin{pmatrix} \eta_x \\ \eta_x' \\ 1 \end{pmatrix}_i \quad (21)$$

[Mathematical 19]

$$\begin{pmatrix} \eta_x \\ \eta_x' \\ 1 \end{pmatrix}_{a2} = M_{a2} \begin{pmatrix} \eta_x \\ \eta_x' \\ 1 \end{pmatrix}_i \quad (22)$$

Next, description will be made about the optical formulae of the charged particles at the beam profile monitor 11b. The optical formulae of the charged particles at the beam profile monitor 11b are also given as similar to the optical formulae of the charged particles at the beam profile monitor 11a.

[Mathematical 20]

$$\begin{pmatrix} \beta_x \\ \alpha_x \\ \gamma_x \end{pmatrix}_b = \begin{pmatrix} m_{11}^2 & -2m_{11}m_{12} & m_{12}^2 \\ -m_{21}m_{11} & 1+2m_{12}m_{21} & -m_{12}m_{22} \\ m_{21}^2 & -2m_{22}m_{21} & m_{22}^2 \end{pmatrix}_b \begin{pmatrix} \beta_x \\ \alpha_x \\ \gamma_x \end{pmatrix}_i \quad (23)$$

The formula (23) shows that the x-direction twiss parameters $\alpha_x$, $\beta_x$, $\gamma_x$ at the start point S are transferred respectively as $\alpha_{xb}$, $\beta_{xb}$, $\gamma_{xb}$ using a transfer matrix $M_{tb}$. When the transfer matrices $M_{a1}$, $M_{a2}$ in the case where excitations of the quadrupole electromagnet 6 and the quadrupole electromagnet 8 are changed are used, namely, when transfer matrices $M_{tb1}$, $M_{tb2}$ for the twiss parameters are used, the x-direction twiss parameters $\alpha_x$, $\beta_x$, $\gamma_x$ are transferred as shown in a formula (24) and a formula (25). Note that the transfer matrix $M_{tb}$ is the matrix in the formula (23) to which the suffix "b" is attached. The suffix "b1" is indicative of a value at the beam profile monitor 11b in the case where the parameters are transferred using the transfer matrix $M_{b1}$ or the transfer matrix $M_{tb1}$, and the suffix "b2" is indicative of a value at the beam profile monitor 11b in the case where the parameters are transferred using the transfer matrix $M_{b2}$ or the transfer matrix $M_{tb2}$.

[Mathematical 21]

$$\begin{pmatrix} \beta_x \\ \alpha_x \\ \gamma_x \end{pmatrix}_{b1} = M_{tb1} \begin{pmatrix} \beta_x \\ \alpha_x \\ \gamma_x \end{pmatrix}_i \quad (24)$$

[Mathematical 22]

$$\begin{pmatrix} \beta_x \\ \alpha_x \\ \gamma_x \end{pmatrix}_{b2} = M_{tb2} \begin{pmatrix} \beta_x \\ \alpha_x \\ \gamma_x \end{pmatrix}_i \quad (25)$$

When the transfer matrix $M_b$ at the beam profile monitor 11b has respective members similar to those in the formula (11), the twiss parameters $\alpha$, $\beta$, $\gamma$ of the beam are transferred as shown in the formula (23). An x-direction beam diameter $r_{xb}$ at the beam profile monitor 11b is represented by a formula (26). $\beta_{xb}$ denotes an x-direction twiss parameter $\beta$ at the beam profile monitor 11b, and $\eta_{xb}$ denotes an x-direction momentum dispersion function at the beam profile monitor 11b. As shown in a formula (29), the x-direction momentum dispersion function $\eta_{xb}$ is obtained from the x-direction momentum dispersion function $\eta_x$ at the start point S after being transferred using the transfer matrix $M_b$ to become $\eta_{xb}$.

[Mathematical 23]

$$r_{xb} = \sqrt{\epsilon_x \beta_{xb}} + \eta_{xb} \cdot \Delta p/p \quad (26)$$

When the transfer matrix $M_{b1}$ in the case where excitations of the quadrupole electromagnet 6 and the quadrupole electromagnet 8 are changed is used, an x-direction beam diameter $r_{xb1}$ at the beam profile monitor 11b is represented by a formula (27), like the case of the formula (26). Meanwhile, when the transfer matrix $M_{b2}$ in the case where excitations of the quadrupole electromagnet 6 and the quadrupole electromagnet 8 are changed is used, an x-direction beam diameter $r_{xb2}$ at the beam profile monitor 11b is represented by a formula (28), like the case of the formula (26). $\beta_{xb1}$ denotes an x-direction twiss parameter $\beta$ at the beam profile monitor 11b having been transferred using the transfer matrix $M_{tb1}$, and $\eta_{xb1}$ denotes an x-direction momentum dispersion function at the beam profile monitor 11b having been transferred using the transfer matrix $M_{b1}$. $\beta_{xb2}$ denotes an x-direction twiss parameter $\beta$ at the beam profile monitor 11b having been transferred using the transfer matrix $M_{tb2}$, and $\eta_{xb2}$ denotes an x-direction momentum dispersion function at the beam profile monitor 11b having been transferred using the transfer matrix $M_{b2}$.

[Mathematical 24]

$$r_{xb1} = \sqrt{\epsilon_x \beta_{xb1}} + \eta_{xb1} \cdot \Delta p/p \quad (27)$$

[Mathematical 25]

$$r_{xb2} = \sqrt{\epsilon_x \beta_{xb2}} + \eta_{xb2} \cdot \Delta p/p \quad (28)$$

A formula (29) shows that the x-direction momentum dispersion function $\eta_x$ at the start point S, and $\eta_x'$ given as its inclination relative to the s-direction, are transferred respectively to become $\eta_{xb}$ and $\eta_{xb}'$ using the transfer matrix $M_b$. When the transfer matrices $M_{b1}$, $M_{b2}$ in the case where excitations of the quadrupole electromagnet 6 and the quadrupole electromagnet 8 are changed are used the x-direction momentum dispersion function $\eta_x$ and the inclination $\eta_x'$ relative to the s-direction, are transferred as shown in a formula (30) and a formula (31).

[Mathematical 26]

$$\begin{pmatrix} \eta_x \\ \eta_x' \\ 1 \end{pmatrix}_b = M_b \begin{pmatrix} \eta_i \\ \eta_i' \\ 1 \end{pmatrix}_i \quad (29)$$

[Mathematical 27]

$$\begin{pmatrix} \eta_x \\ \eta_x' \\ 1 \end{pmatrix}_{b1} = M_{b1} \begin{pmatrix} \eta_i \\ \eta_i' \\ 1 \end{pmatrix}_i \quad (30)$$

[Mathematical 28]

$$\begin{pmatrix} \eta_x \\ \eta_x' \\ 1 \end{pmatrix}_{b2} = M_{b2} \begin{pmatrix} \eta_i \\ \eta_i' \\ 1 \end{pmatrix}_i \quad (31)$$

In Step S14, from the above shown optical formulae of the charged particles at the beam profile monitors 11a, 11b and a formula (32), twiss parameters ($\alpha_{xi}$, $\beta_{xi}$, $\gamma_{xi}$) and momentum dispersion functions ($\eta_{xi}$, $\eta_{xi}'$) at the start point S are calculated. Using them as an initial condition, by the optical parameter calculator 17, such optical parameters are calculated that afford an optical condition (Condition 2) in which the beam diameter is not enlarged at the terminal point T, namely, the beam diameter becomes the same as the beam diameter at the irradiation position (terminal point T) at the time of detecting the profile data by the beam profile monitors 11. The optical parameters that satisfy this Condition 2 are outputted to the device controller 16.

[Mathematical 29]

$$\beta_i \gamma_i - \alpha_i^2 = 1 \quad (32)$$

In Step S15, for the second time, the device controller 16 sends the current values based on the optical parameters that afford Condition 2 to the electromagnet power source 15, to thereby set a specified current for each of the electromagnets.

When the respective electromagnets are set to the current values in Step S15, the beam diameter becomes small at the irradiation position (terminal point T) as shown in FIG. 11 and FIG. 12. In a state where no correction is made to nearly nullify the chromatic aberration at the terminal point T, even at the downstream side of the beam profile monitor 11b, the beam diameter becomes larger as shown by circles 47d, 47f, 47g, than the beam diameter at the start point S (circle 47a). However, after correction is made to nearly nullify the chromatic aberration at the terminal point T, at the downstream side of the beam profile monitor 11b, the beam diameter is, as shown by circles 49d to 49g, nearly the same as the beam diameter at the start point S (circle 49a), so that the beam diameter at the irradiation position (terminal point T) becomes smaller than that before correction.

The beam transport system 4 of Embodiment 2 can nearly nullify the chromatic aberration of the beam at the beam irradiation position (terminal point T), and thus, at the time the charged particle beam is subjected to beam emission from the accelerator 3 by an RF knockout method, it can suppress the beam diameter from being enlarged due to the chromatic aberration, to thereby achieve a small diameter beam at the irradiation position (terminal point T).

Even in the case with a small-sized synchrotron, and even when the chromatic aberration is not nullified at the start point S in the optical parameter design of the beam transport system 4 using a high-performance bending electromagnet, quadrupole electromagnet or six-pole electromagnet, the beam transport system 4 of Embodiment 2 can nearly nullify (set to substantially zero) the chromatic aberration of the beam at the irradiation position of the charged particle beam 31. Accordingly, the beam transport system 4 of Embodiment 2, even in the case with a small-sized synchrotron, can avoid bringing enlargement or complexity of the accelerator or the beam transport system, to thereby suppress the accelerator and the beam transport system from becoming significantly expensive.

The design methodology of the beam transport system 4 shown in Embodiment 2 is such that: in the beam transport system being set to an ideal magnetic field condition for the case where the charged particle beam is subjected to beam emission from the accelerator 3 by an RF knockout method, the beam sizes (beam diameters) in the middle of the beam transport system 4 are measured using profile data detected by the beam profile monitors 11; the x-direction momentum dispersion functions $\eta x$, $\eta x'$ and the y-direction momentum dispersion functions $\eta y$, $\eta y'$ that are a part of the initial condition at the beam communication point (start point S), are calculated as the start-point momentum dispersion functions; and new optical parameters for the beam transport system 4 are set using, as the initial condition, the above Condition 2 that is the beginning condition at the irradiation position (terminal point T) at the time of detecting the profile data, and the start-point momentum dispersion functions. When this design methodology is applied, the adjustment becomes easy even at the installation site. Thus, as differed from a method in which the adjustment has to be made many times like a conventional case, it is possible to reduce the time for the adjustment of the beam transport system in comparison to the conventional case.

For the case where the chromatic aberration in the x-direction of the charged particle beam 31 at the irradiation position (terminal point T) is nearly nullified to thereby suppress an increase of the beam size, one or more bending electromagnets 7 for causing deflection in the x-direction is placed and two or more quadrupole electromagnets 8 for controlling focusing/defocusing in the x-direction are placed upstream of that bending electromagnet 7. In FIG. 11 and FIG. 12, the bending electromagnet 7b and the quadrupole electromagnets 8a, 8b are the requisite minimum ones among the bending electromagnets 7 and the quadrupole electromagnets 8. Meanwhile, for the case where the chromatic aberration in the y-direction of the charged particle beam 31 at the irradiation position (terminal point T) is nearly nullified to thereby suppress an increase of the beam size, one or more bending electromagnets 7 for causing deflection in the y-direction is placed and two or more quadrupole electromagnets 8 for controlling focusing/defocusing in the y-direction are placed upstream of that bending electromagnet 7.

In FIG. 1, FIG. 11 and FIG. 12, although the bending electromagnet 7 for causing deflection in the y-direction is not illustrated in the beam transport system 4, it suffices that: it is placed, for example, at the downstream side of the bending electromagnet 7b; and two of the quadrupole electromagnets 8 placed upstream of the bending electromagnet 7 for causing deflection in the y-direction are each set to serve as a quadrupole electromagnet for controlling focusing/defocusing in the y-direction. In the example of FIG. 1, the circulating charged particle beam 31 is introduced into the beam transport system 4 by being moved in the x-direction, so that a y-direction chromatic aberration at the start point S can be made sufficiently small by the bending electromagnets 5 and the quadrupole electromagnets 6 placed in the accelerator 3. Thus, with respect to the y-direction bending electromagnet 7 and quadrupole electromagnets 8 for nearly nullifying the chromatic aberration in the y-direction of the charged particle beam 31 at the irradiation position (terminal point T), thereby suppressing an increase of the beam size, they just have to be placed when the chromatic aberration in the y-direction at the start point S is large.

Embodiment 3

Figure 13:
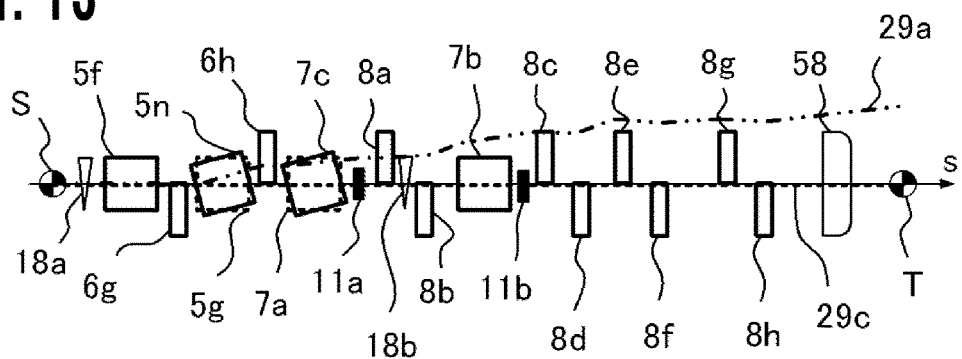
FIG. 13 is a diagram showing beam trajectories before correction in a beam transport system according to Embodiment 3 of the invention.
Figure 14:
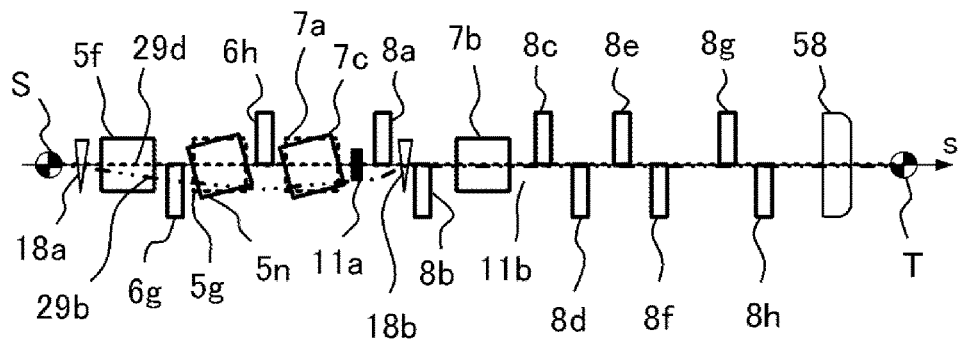
FIG. 14 is a diagram showing beam trajectories after correction in the beam transport system according to Embodiment 3 of the invention.
Figure 15:
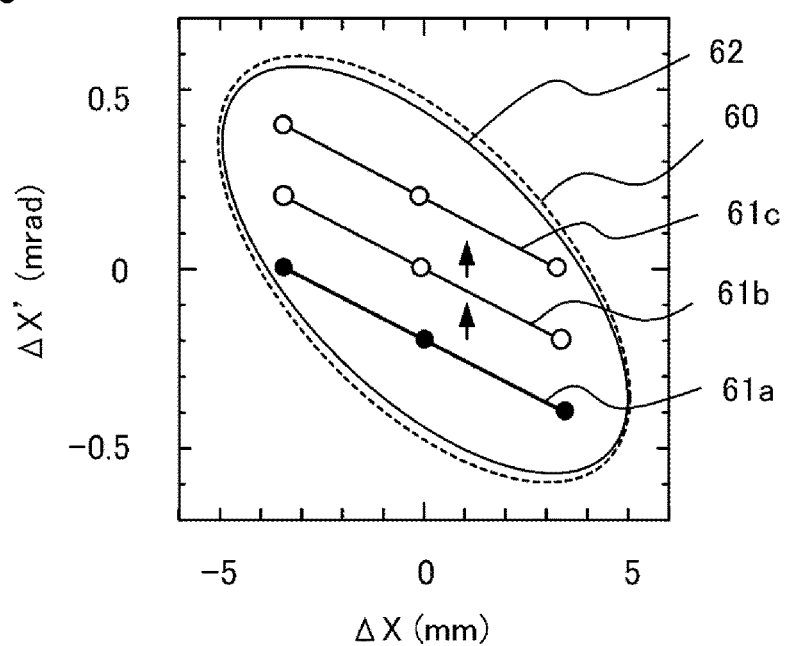
FIG. 15 is a graph illustrating a movement of a beam in a phase space at a start point.
Figure 16:
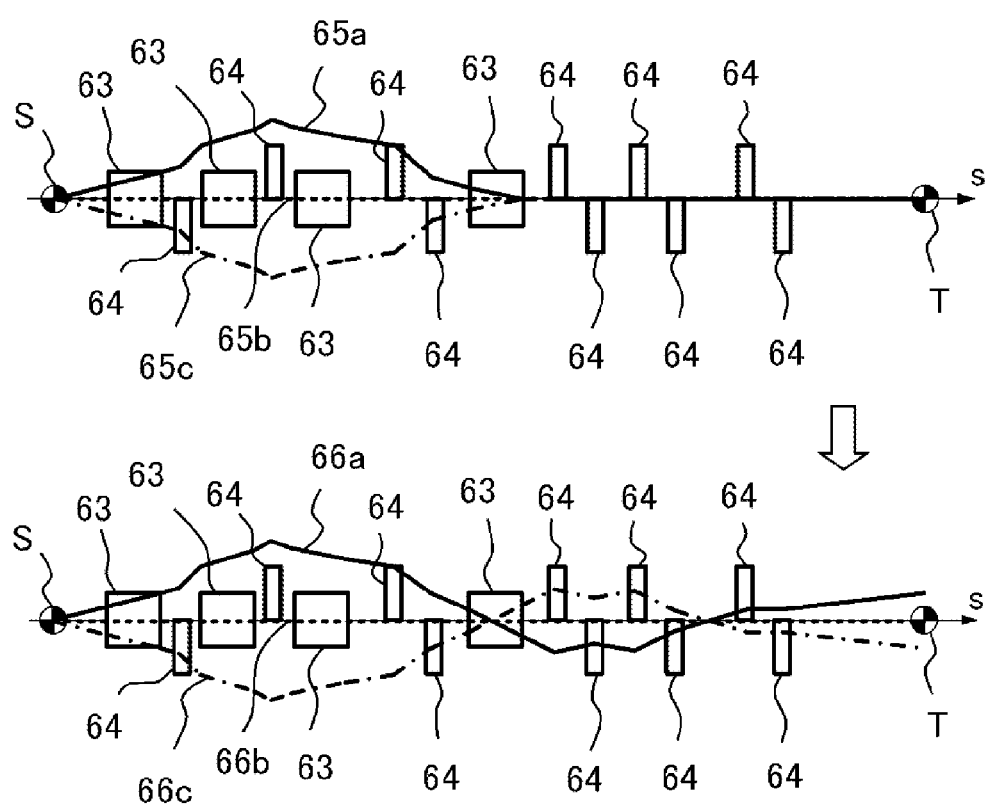
FIG. 16 is diagrams each illustrating beam trajectories in a beam transport system.

In Embodiment 1 and Embodiment 2, the chromatic aberration in the x-direction of the charged particle beam 31 is nearly nullified at the irradiation position (terminal point T). In Embodiment 3, such a beam transport system 4 will be described that causes the charged particle beam 31 not to move in the x-direction at the irradiation position (terminal point T) even if the chromatic aberration in the x-direction of the charged particle beam 31 is not nearly nullified at the irradiation position (terminal point T). FIG. 13 is a diagram showing beam trajectories before correction in the beam transport system according to Embodiment 3 of the invention, and FIG. 14 is a diagram showing beam trajectories after correction in the beam transport system according to Embodiment 3 of the invention. FIG. 13 corresponds to FIG. 4 provided that the bending electromagnets 5g, 7a are instead placed in an inclined manner as bending electromagnets 5n, 7c, and steering electromagnets 18a, 18b are added. FIG. 14 corresponds to FIG. 4 provided that the bending electromagnets 5g, 7a are instead placed in an inclined manner as bending electromagnets 5n, 7c, and steering electromagnets 18a, 18b are added. Note that in FIG. 13 and FIG. 14, the bending electromagnets 5g, 7a are indicated by broken lines. In FIG. 13 and FIG. 14, the bending electromagnets 5n, 7c placed in an inclined manner are indicative of occurrence of placement errors of the electromagnets due to displacement from the position at the design.

When there are placement errors at the bending electromagnets 5n, 7c, this results in a state as shown by the beam trajectory 29a in FIG. 13, even in the beam transport system 4 to which the design methodology of the beam transport system 4 of Embodiment 1 or the design methodology of the beam transport system 4 of Embodiment 2 is applied. Thus, the charged particle beam 31 comes to a deviated position at the irradiation position (terminal point T). In Embodiment 3, because of the addition of the steering electromagnets 18a, 18b, the placement errors of the bending electromagnets in the beam transport system 4 can be corrected to thereby afford a state as shown by the beam trajectory 29b in FIG. 14, so that the beam position at the irradiation position (terminal point T) can be matched accurately to an irradiation position at the time of no operation of the particle beam irradiation apparatus 58 (isocenter). In this case, it is possible to nearly nullify the chromatic aberration in the x-direction of the charged particle beam 31 at the irradiation position (terminal point T). Note that a beam trajectory 29c is another beam trajectory before correction in the case with the bending electromagnets 5g, 7a indicated by the broken lines. A beam trajectory 29d is another beam trajectory after correction in the case with the bending electromagnets 5g, 7a indicated by the broken lines.

Such a fact that the beam trajectory 29b in FIG. 14 can be afforded even when there are placement errors at the bending electromagnets 5n, 7c in the beam transport system 4, shows that it is possible to cause the charged particle beam 31 not to move in the x-direction at the irradiation position (terminal point T) even when there is no placement error at the bending electromagnets 5n, 7c and instead the chromatic aberration in the x-direction of the charged particle beam 31 is somewhat large at the irradiation position (terminal point T). Accordingly, the beam transport system 4 of Embodiment 3 can cause the charged particle beam 31 not to move in the x-direction at the irradiation position (terminal point T), even if the chromatic aberration in the x-direction of the charged particle beam 31 is not nearly nullified at the irradiation position (terminal point T), and is thus effective when it is difficult at the irradiation position (terminal point T) to adjust the chromatic aberration in the x-direction of the charged particle beam 31.

Note that the particle beam therapy system 20 to which the beam transport system 4 of Embodiment 3 is applied, corresponds to FIG. 1 provided that the steering electromagnets 18a, 18b are added at the positions shown in FIG. 13 and FIG. 14.

It should be noted that any combination of the respective embodiments and any appropriate modification or omission in the embodiments may be made in the present invention without departing from the scope of the invention.

DESCRIPTION OF REFERENCE NUMERALS AND SIGNS

3: accelerator, 4: beam transport system, 7, 7a, 7b: bending electromagnets, 8, 8a, 8b, 8c, 8d, 8e, 8f, 8g, 8h: quadrupole electromagnets, 9: acceleration cavity, 10: x-direction kick electrode, 11, 11a, 11b: beam profile monitors, 14: beam analyzer, 15: electromagnet power source, 17: optical parameter calculator, 18a, 18b: steering electromagnets, 20: particle beam therapy system, 31: charged particle beam, 45: irradiation target, 58: particle beam irradiation apparatus, S: start point (start point in design), T: terminal point (irradiation position), $\eta$, $\eta'$, $\eta x$, $\eta x'$, $\eta y$, $\eta y'$: momentum dispersion functions.

The invention claimed is:

1. A beam transport system for transporting a charged particle beam emitted from an accelerator to an irradiation position, comprising:
at least one bending electromagnet that deflects the charged particle beam;
at least two quadrupole electromagnets that focus or defocus the charged particle beam;
at least one beam profile monitor that detects profile data of the charged particle beam;
a beam analyzer that calculates based on the profile data, a beam temporal-variation related amount that is a beam-position temporal variation amount or a beam diameter, at the beam profile monitor;
an optical parameter calculator that calculates optical parameters of the beam transport system; and
an electromagnet power source that sets an excitation current of each of the bending electromagnet and the quadrupole electromagnets, based on the optical parameters calculated by the optical parameter calculator;
wherein the optical parameter calculator: calculates based on the beam temporal-variation related amount, a start-point momentum dispersion function that is a momentum dispersion function of the charged particle beam at a start point in design of the beam transport system that is set on a beam trajectory of the accelerator; and
calculates said optical parameters using, as an initial condition, the start-point momentum dispersion function and a beginning condition at the irradiation position at the time of detecting the profile data.

2. The beam transport system of claim 1, wherein:
the accelerator is a synchrotron; and
when the charged particle beam is emitted from the accelerator by sweeping high-frequency power supplied to an acceleration cavity placed in the accelerator, the beam analyzer calculates, as the beam temporal-variation related amount, the beam-position temporal variation amount at the beam profile monitor.

3. The beam transport system of claim 1, wherein the beginning condition includes such a condition that a terminal-point momentum dispersion function that is a momentum dispersion function of the charged particle beam at the irradiation position is equal to zero.

4. The beam transport system of claim 1, wherein:
the accelerator is a synchrotron; and
when the charged particle beam is emitted from the accelerator by supplying high-frequency power to a kick electrode placed in the accelerator to thereby increase an emittance on a circulating plane of the charged particle beam and in a direction perpendicular to a traveling direction of the charged particle beam and, the beam analyzer calculates, as the beam temporal-variation related amount, the beam diameter at the beam profile monitor.

5. The beam transport system of claim 1, wherein the beginning condition includes a setup condition of the beam diameter of the charged particle beam at the irradiation position.

6. The beam transport system of claim 1, further comprising a steering electromagnet for correcting a placement error of the bending electromagnet.

7. A particle beam therapy system comprising:
an accelerator that accelerates a charged particle beam;
a beam transport system that transports the charged particle beam emitted from the accelerator to an irradiation position; and
a particle beam irradiation apparatus that is placed at a downstream side of the beam transport system and that radiates the charged particle beam to an irradiation target so as to form an intended irradiation field;
wherein said beam transport system is the beam transport system of claim 1.

8. The beam transport system of claim 2, wherein the beginning condition includes such a condition that a terminal-point momentum dispersion function that is a momentum dispersion function of the charged particle beam at the irradiation position is equal to zero.

9. The beam transport system of claim 4, wherein the beginning condition includes a setup condition of the beam diameter of the charged particle beam at the irradiation position.

10. The beam transport system of claim 2, further comprising a steering electromagnet for correcting a placement error of the bending electromagnet.

11. The beam transport system of claim 3, further comprising a steering electromagnet for correcting a placement error of the bending electromagnet.

12. The beam transport system of claim 4, further comprising a steering electromagnet for correcting a placement error of the bending electromagnet.

13. The beam transport system of claim 5, further comprising a steering electromagnet for correcting a placement error of the bending electromagnet.

14. A particle beam therapy system comprising:
an accelerator that accelerates a charged particle beam;
a beam transport system that transports the charged particle beam emitted from the accelerator to an irradiation position; and
a particle beam irradiation apparatus that is placed at a downstream side of the beam transport system and that radiates the charged particle beam to an irradiation target so as to form an intended irradiation field;
wherein said beam transport system is the beam transport system of claim 2.

15. A particle beam therapy system comprising:
an accelerator that accelerates a charged particle beam;
a beam transport system that transports the charged particle beam emitted from the accelerator to an irradiation position; and
a particle beam irradiation apparatus that is placed at a downstream side of the beam transport system and that radiates the charged particle beam to an irradiation target so as to form an intended irradiation field;
wherein said beam transport system is the beam transport system of claim 3.

16. A particle beam therapy system comprising:
an accelerator that accelerates a charged particle beam;
a beam transport system that transports the charged particle beam emitted from the accelerator to an irradiation position; and
a particle beam irradiation apparatus that is placed at a downstream side of the beam transport system and that radiates the charged particle beam to an irradiation target so as to form an intended irradiation field;
wherein said beam transport system is the beam transport system of claim 4.

17. A particle beam therapy system comprising:
an accelerator that accelerates a charged particle beam;
a beam transport system that transports the charged particle beam emitted from the accelerator to an irradiation position; and
a particle beam irradiation apparatus that is placed at a downstream side of the beam transport system and that radiates the charged particle beam to an irradiation target so as to form an intended irradiation field;
wherein said beam transport system is the beam transport system of claim 5.

18. A particle beam therapy system comprising:
an accelerator that accelerates a charged particle beam;
a beam transport system that transports the charged particle beam emitted from the accelerator to an irradiation position; and
a particle beam irradiation apparatus that is placed at a downstream side of the beam transport system and that radiates the charged particle beam to an irradiation target so as to form an intended irradiation field;
wherein said beam transport system is the beam transport system of claim 6.

* * * * *